United States Patent
Annoni et al.

(10) Patent No.: US 10,675,469 B2
(45) Date of Patent: Jun. 9, 2020

(54) PAIN MANAGEMENT BASED ON BRAIN ACTIVITY MONITORING

(71) Applicant: Boston Scientific Neuromodulation Corporation, Valencia, CA (US)

(72) Inventors: Elizabeth Mary Annoni, White Bear Lake, MN (US); Jianwen Gu, Valencia, CA (US); Rosana Esteller, Marietta, GA (US); Bryan Allen Clark, Forest Lake, MN (US); Pramodsingh Hirasingh Thakur, Woodbury, MN (US); Kyle Harish Srivastava, Saint Paul, MN (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 203 days.

(21) Appl. No.: 15/867,801

(22) Filed: Jan. 11, 2018

(65) Prior Publication Data

US 2018/0193651 A1 Jul. 12, 2018

Related U.S. Application Data

(60) Provisional application No. 62/445,061, filed on Jan. 11, 2017.

(51) Int. Cl.
*A61N 1/00* (2006.01)
*A61N 1/36* (2006.01)
(Continued)

(52) U.S. Cl.
CPC ...... *A61N 1/36139* (2013.01); *A61B 5/04008* (2013.01); *A61B 5/0476* (2013.01);
(Continued)

(58) Field of Classification Search
CPC ............ A61N 1/36139; A61N 1/36185; A61N 1/36071; A61N 1/36062; A61N 1/0551;
(Continued)

(56) References Cited

U.S. PATENT DOCUMENTS 4,297,685 A 10/1981 Brainard, II
5,187,675 A 2/1993 Dent et al.
(Continued)

FOREIGN PATENT DOCUMENTS

EP 1059064 A2 12/2000
EP 1897586 A1 3/2008
(Continued)

OTHER PUBLICATIONS

"2015 Sleep in America® Poll Sleep and Pain—Summary of Findings", National Sleep Foundation, (2015), 1-54.
(Continued)

*Primary Examiner* — Mallika D Fairchild
(74) *Attorney, Agent, or Firm* — Schwegman Lundberg & Woessner, P.A.

(57) ABSTRACT

This document discusses, among other things, systems and methods for managing pain of a subject. A system includes one or more physiological sensors configured to sense a physiological signal indicative of patient brain activity. The physiological signals may include an electroencephalography signal, a magnetoencephalography signal, or a brain-evoked potential. The system may extract from the brain activity signal one or more signal metrics indicative of strength or pattern of brain electromagnetic activity associated with pain, and generate a pain score using the one or more signal metrics. The pain score can be output to a patient or a process. The system may select an electrode configuration for pain-relief electrostimulation based on the
(Continued)

pain score, and deliver a closed-loop pain therapy according to the selected electrode configuration.

20 Claims, 6 Drawing Sheets

(51) Int. Cl.
| | | |
|---|---|---|
| *A61B 5/0478* | (2006.01) | |
| *A61B 5/00* | (2006.01) | |
| *A61B 5/04* | (2006.01) | |
| *A61B 5/0484* | (2006.01) | |
| *A61B 5/0476* | (2006.01) | |
| *A61N 1/05* | (2006.01) | |

(52) U.S. Cl.
CPC .......... *A61B 5/0478* (2013.01); *A61B 5/0484* (2013.01); *A61B 5/4824* (2013.01); *A61B 5/4836* (2013.01); *A61N 1/36071* (2013.01); *A61N 1/36185* (2013.01); *A61B 5/4848* (2013.01); *A61N 1/0534* (2013.01); *A61N 1/0551* (2013.01); *A61N 1/36062* (2017.08)

(58) Field of Classification Search
CPC .. A61N 1/0534; A61B 5/0484; A61B 5/4836; A61B 5/04008; A61B 5/4824; A61B 5/0478; A61B 5/0476; A61B 5/4848
See application file for complete search history.

(56) References Cited

U.S. PATENT DOCUMENTS

| | | | |
|---|---|---|---|
| 5,774,591 | A | 6/1998 | Black et al. |
| 6,016,103 | A | 1/2000 | Leavitt |
| 6,076,011 | A | 6/2000 | Hoover |
| 6,088,040 | A | 7/2000 | Oda et al. |
| 6,173,260 | B1 | 1/2001 | Slaney |
| 6,480,734 | B1 | 11/2002 | Zhang et al. |
| 6,497,658 | B2 | 12/2002 | Roizen et al. |
| 6,654,632 | B2 | 11/2003 | Lange et al. |
| 6,659,968 | B1 | 12/2003 | McClure |
| 6,731,984 | B2 | 5/2004 | Cho et al. |
| 6,871,099 | B1 | 3/2005 | Whitehurst et al. |
| 7,001,337 | B2 | 2/2006 | Dekker |
| 7,004,907 | B2 | 2/2006 | Banet et al. |
| 7,177,686 | B1 | 2/2007 | Turcott |
| 7,189,204 | B2 | 3/2007 | Ni et al. |
| 7,222,075 | B2 | 5/2007 | Petrushin |
| 7,299,086 | B2 | 11/2007 | McCabe et al. |
| 7,376,457 | B2 | 5/2008 | Ross |
| 7,407,485 | B2 | 8/2008 | Huiku |
| 7,463,927 | B1 | 12/2008 | Chaouat |
| 7,566,308 | B2 | 7/2009 | Stahmann |
| 7,627,475 | B2 | 12/2009 | Petrushin |
| 7,636,602 | B2 | 12/2009 | Baru Fassio et al. |
| 7,650,184 | B2 | 1/2010 | Walter |
| 7,678,061 | B2 | 3/2010 | Lee et al. |
| 7,775,993 | B2 | 8/2010 | Heruth et al. |
| 7,957,809 | B2 | 6/2011 | Bourget et al. |
| 7,986,991 | B2 | 7/2011 | Prichep |
| 8,019,439 | B2 | 9/2011 | Kuzma et al. |
| 8,055,348 | B2 | 11/2011 | Heruth et al. |
| 8,083,682 | B2 | 12/2011 | Dalal et al. |
| 8,192,376 | B2 | 6/2012 | Lovett et al. |
| 8,209,182 | B2 | 6/2012 | Narayanan |
| 8,290,596 | B2 | 10/2012 | Wei et al. |
| 8,332,038 | B2 | 12/2012 | Heruth et al. |
| 8,398,556 | B2 | 3/2013 | Sethi et al. |
| 8,447,401 | B2 | 5/2013 | Miesel et al. |
| 8,475,370 | B2 | 7/2013 | McCombie et al. |
| 8,529,459 | B2 | 9/2013 | Malker et al. |
| 8,606,356 | B2 | 12/2013 | Lee et al. |
| 8,688,221 | B2 | 4/2014 | Miesel |
| 8,744,587 | B2 | 6/2014 | Miesel et al. |

| | | | |
|---|---|---|---|
| 8,805,518 | B2 | 8/2014 | King et al. |
| 9,066,659 | B2 | 6/2015 | Thakur et al. |
| 9,072,870 | B2 | 7/2015 | Wu et al. |
| 9,119,965 | B2 | 9/2015 | Xi et al. |
| 9,314,168 | B2 | 4/2016 | Watson et al. |
| 9,395,792 | B1 | 7/2016 | Kahn et al. |
| 2004/0015091 | A1 | 1/2004 | Greenwald et al. |
| 2005/0209643 | A1 | 9/2005 | Heruth et al. |
| 2007/0167859 | A1 | 7/2007 | Finneran et al. |
| 2007/0213783 | A1* | 9/2007 | Pless ................. A61N 1/36071 607/42 |
| 2007/0260285 | A1 | 11/2007 | Libbus et al. |
| 2008/0177191 | A1 | 7/2008 | Patangay et al. |
| 2008/0249430 | A1 | 10/2008 | John et al. |
| 2009/0124863 | A1 | 5/2009 | Liu et al. |
| 2009/0192556 | A1 | 7/2009 | Wu et al. |
| 2009/0312663 | A1 | 12/2009 | John et al. |
| 2009/0318986 | A1 | 12/2009 | Alo et al. |
| 2010/0016913 | A1 | 1/2010 | Arcot-Krishnamurthy et al. |
| 2010/0286549 | A1 | 11/2010 | John et al. |
| 2011/0015702 | A1 | 1/2011 | Ternes et al. |
| 2011/0021928 | A1 | 1/2011 | Giovangrandi et al. |
| 2011/0112420 | A1 | 5/2011 | Nagata et al. |
| 2011/0124979 | A1 | 5/2011 | Heneghan et al. |
| 2011/0137134 | A1 | 6/2011 | Hemmerling et al. |
| 2011/0172562 | A1 | 7/2011 | Sahasrabudhe et al. |
| 2011/0224749 | A1 | 9/2011 | Ben-David et al. |
| 2011/0306846 | A1 | 12/2011 | Osorio |
| 2012/0109012 | A1 | 5/2012 | Cinbis |
| 2013/0165994 | A1 | 6/2013 | Ternes et al. |
| 2013/0268016 | A1 | 10/2013 | Xi et al. |
| 2014/0276188 | A1 | 9/2014 | Jardin |
| 2014/0276549 | A1* | 9/2014 | Osorio ................. A61M 5/1723 604/503 |
| 2015/0005842 | A1* | 1/2015 | Lee .................... A61N 1/36164 607/46 |
| 2015/0025335 | A1 | 1/2015 | Jain et al. |
| 2015/0289803 | A1 | 10/2015 | Wu et al. |
| 2016/0022203 | A1 | 1/2016 | Arnold et al. |
| 2016/0082265 | A1* | 3/2016 | Moffitt ............... A61N 1/36021 607/46 |
| 2016/0129272 | A1 | 5/2016 | Hou et al. |
| 2016/0144194 | A1* | 5/2016 | Roothans ........... A61N 1/37247 607/45 |
| 2016/0243359 | A1 | 8/2016 | Sharma |
| 2016/0302720 | A1* | 10/2016 | John .................... A61B 5/0476 |
| 2016/0350509 | A1 | 12/2016 | Sharma |
| 2016/0374567 | A1 | 12/2016 | Breslow et al. |
| 2017/0136264 | A1 | 5/2017 | Hyde et al. |
| 2017/0165485 | A1 | 6/2017 | Sullivan et al. |
| 2018/0078768 | A1 | 3/2018 | Thakur et al. |
| 2018/0085055 | A1 | 3/2018 | Annoni et al. |
| 2018/0085584 | A1 | 3/2018 | Thakur et al. |
| 2018/0110464 | A1 | 4/2018 | Annoni et al. |
| 2018/0192941 | A1 | 7/2018 | Annoni et al. |
| 2018/0192942 | A1 | 7/2018 | Clark et al. |
| 2018/0192943 | A1 | 7/2018 | Annoni et al. |
| 2018/0193644 | A1 | 7/2018 | Annoni et al. |
| 2018/0193650 | A1 | 7/2018 | Srivastava et al. |
| 2018/0193652 | A1 | 7/2018 | Srivastava et al. |
| 2018/0229040 | A1 | 8/2018 | Srivastava et al. |

FOREIGN PATENT DOCUMENTS

| | | |
|---|---|---|
| RU | 2559783 C1 | 8/2015 |
| WO | WO-2007007058 A1 | 1/2007 |
| WO | WO-2009055127 A1 | 4/2009 |
| WO | WO-2010051406 A1 | 5/2010 |
| WO | WO-2011008747 A2 | 1/2011 |
| WO | WO-2011053607 A1 | 5/2011 |
| WO | WO-2013134479 A1 | 9/2013 |
| WO | WO-2014151860 A1 | 9/2014 |
| WO | WO-2015060888 A1 | 4/2015 |
| WO | WO-2015128567 | 9/2015 |
| WO | WO-2016025989 A1 | 2/2016 |
| WO | WO-2016077786 A1 | 5/2016 |
| WO | WO-2018052695 A1 | 3/2018 |

(56) References Cited

FOREIGN PATENT DOCUMENTS

| WO | WO-2018063637 A1 | 4/2018 |
|---|---|---|
| WO | WO-2018063912 A1 | 4/2018 |
| WO | WO-2018080887 A1 | 5/2018 |

OTHER PUBLICATIONS

"International Application Serial No. PCT/US2017/048867, International Search Report dated Nov. 13, 2017", 5 pgs.

"International Application Serial No. PCT/US2017/048867, Written Opinion dated Nov. 13, 2017", 6 pgs.

"International Application Serial No. PCT/US2017/048896, International Search Report dated Nov. 27, 2017", 5 pgs.

"International Application Serial No. PCT/US2017/048896, Written Opinion dated Nov. 27, 2017", 6 pgs.

"International Application Serial No. PCT/US2017/052685, International Search Report dated Jan. 4, 2018", 5 pgs.

"International Application Serial No. PCT/US2017/052685, Written Opinion dated Jan. 4, 2018", 6 pgs.

Ahern, David K., et al., "Comparison of lumbar paravertebral EMG patterns in chronic low back pain patients and non-patient controls", Pain, 34, (1988), 153-160.

Allum, John H.J., et al., "A speedy solution for balance and gait analysis: angular velocity measured at the centre of body mass", Current Opinion in Neurology 18, (2005), 15-21.

Alo, Kenneth M., et al., "Effect of Spinal Cord Stimulation on Sensory Nerve Conduction Threshold Functional Measures", Neuromodulation, vol. 3, No. 3, (2000), 145-154.

Ambady, Nalini, et al., "Thin Slices of Expressive Behavior as Predictors of Interpersonal Consequences: A Meta-Analysis", Psychological Bulletin, 1992, vol. 111, No. 2, 256-274.

Annoni, Elizabeth M., et al., "Method and Apparatus for Pain Management Using Objective Pain Measure", U.S. Appl. No. 62/400,336, filed Sep. 27, 2016.

Annoni, Elizabeth M., et al., "Pain Management Based on Brain Activity Monitoring", U.S. Appl. No. 62/445,061, filed Jan. 11, 2017.

Annoni, Elizabeth M., et al., "Pain Management Based on Muscle Tension Measurements", U.S. Appl. No. 62/445,092, filed Jan. 11, 2017.

Annoni, Elizabeth M., et al., "Pain Management Based on Respiration-Mediated Heart Rates", U.S. Appl. No. 62/445,069, filed Jan. 11, 2017.

Annoni, Elizabeth M., et al., "Patient-Specific Calibration of Pain Quantification", U.S. Appl. No. 62/445,095, filed Jan. 11, 2017.

Arsenault, Marianne, et al., "Pain Modulation Induced by Respiration: Phase and Frequency Effects", Neuroscience 252, (2013), 501-511.

Artner, Juraj, et al., "Prevalence of sleep deprivation in patients with chronic neck and back pain: a retrospective evaluation of 1016 patients", Journal of Pain Research: 6, (2013), 1-6.

Bakker, Jorn, et al., "What's your current stress level? Detection of stress patterns from Gsr sensor data", Eindhoven University of Technology—The Netherlands, (2011), 1-8.

Baliki, Marwan N., et al., "Beyond Feeling: Chronic Pain hurts the Brain, Disrupting the Default-Mode Network Dynamics", The Journal of Neuroscience, 28 (6), (Feb. 6, 2008), 1398-1403.

Banos, Oresti, et al., "PhysioDroid: Combining Wearable Health Sensors and Mobile Devices for a Ubiquitous, Continuous, and Personal Monitoring", The Scientific World Journal, vol. 2014 Article ID 190824, (2014), 11 pgs.

Bansevicius, Dalius, et al., "Mental stress of long duration: EMG activity, perceived tension, fatigue, and pain development in pain-free subjects", Headache: The Journal of Head and Face Pain; 37.8, (1997), 499-510.

Barad, Meredith J., et al., "Complex Regional Pain Syndrome is Associated With Structural Abnormalities in Pain-Related Regions of the Human Brain", The Journal of Pain, vol. 15, No. 2, (Feb. 2914), 197-203.

Barkley, Jacob E., et al., "The effect of spinal cord stimulation unit revision on perceived pain, anxiety, mobility and physical activity in individuals with low back/lower extremity pain", Kent State University—The Spine and Pain Institute, Presented at Annual Meeting of the North American Neuromodulation Society (NANS) on Dec. 11-14, 2014, 1 pg.

Bartlett, Marian Stewart, et al., "Automatic Decoding of Facial Movements Reveals Deceptive Pain Expressions", Current Biology 24, 738-743, Mar. 31, 2014.

Beneck, George J., et al., "Spectral analysis of EMG using intramuscular electrodes reveals non-linear fatigability characteristics in persons with chronic low back pain", Journal of Electromyography and Kinesiology 23, (2013), 70-77.

Ben-Israel, Nir, et al., "Monitoring the nociception level: a multi-parameter approach", J Clin Monit Comput, (Jul. 2012), 10 pgs.

Ben-Israel, Nir, et al., "Monitoring the nociception level: a multi-parameter approach", J Clin Monit Comput 27, (2013), 659-668.

Boselli, E., et al., "Prediction of immediate postoperative pain using the analgesia/ nociception index: a prospective observational study", British Journal of Anaesthesia 112 (4):, (2014), 715-721.

Boselli, E., et al., "Prospective observational study of the non-invasive assessment of immediate postoperative pain using the analgesia/nociception index (ANI)", British Journal of Anaesthesia 111, (2013), 453-459.

Broucqsault-Dédrie, Celine, et al., "Measurement of Heart Rate Variability to Assess Pain in Sedated Critically Ill Patients: A Prospective Observational Study", PLOS One, (Jan. 25, 2016), 1-11.

Chan, C. W.Y., et al., "Subjective pain sensation is linearly correlated with the Flexion reflex in man", Brain Research, 479, (1989), 145-150.

Chapman, C. Richard, et al., "Phasic pupil dilation response to noxious stimulation in normal volunteers: relationship to brain evoked potentials and pain report", (1999), 44-52.

Chen, Shuzhen, et al., "The role of the autonomic nervous system in hypertension: a bond graph model study", Physiological measurement 29.4 (2008): 473, (2008), 473-495.

Cheng, Qian, et al., "GaitTrack: Health Monitoring of Body Motion from Spatio-Temporal Parameters of Simple Smart Phones", The ACM Conference on Bioinformatics, Computational Biology, Biomed Biomedical Informatics (BCB) Health Information Symposium (HIS), Sep. 25, 2013,, (2013) 1-10.

Chuang, Chiung-Cheng, et al., "Photoplethysmography variability as an alternative approach to obtain heart rate variability information in chronic pain patient", J Clin Monit Comput—Published online, (Feb. 24, 2015), 1-6.

Chung, Ok Y., "Baroreflex sensitivity associated hypoalgesia in healthy states is altered by chronic pain", Pain 138, (2008), 87-97.

Ciampi De Andrade, Daniel, et al., "Neurophysiological assessment of spinal cord stimulation in failed back surgery syndrome", Pain 150, (2010), 485-491.

Cinaz, Burcu, et al., "Monitoring of mental workload levels during an everyday life office-work scenario", Pers Ubiquit Comput 17, (2013), 229-239.

Clark, Bryan Allen, et al., "Pain Management Based on Functional Measurements", U.S. Appl. No. 62/445,075, filed Jan. 11, 2017.

Culic, Ognjen, et al., "Serum activities of adenosine deaminase, dipeptidyl peptidase IV and prolyl endopeptidase in patients with fibromyalgia:diagnostic implications", Clin Rheumatol 35, (2016), 2565-2571.

Dansie, Elizabeth J., et al., "Activity in Adults with Chronic Widespread Pain", The Journal of Pain—Accepted Manuscript, (2014), 33 pgs.

Davydov, Dmitry M., et al., "Cardiovascular activity and chronic pain severity", Physiology & Behavior 152, 203-216 (2015).

De-La-Herran, Alvaro M., et al., "Gait Analysis Methods: An Overview of Wearable and Non-Wearable Systems, Highlighting Clinical Applications", Sensors 14, (2014), 3362-3394.

Denk, Franziska, et al., "Chronic Pain: Emerging Evidence for the Involvement of Epigenetics", Neuron 73 (3), (2012), 435-444.

Duschek, S., "Relationship between baroreceptor cardiac reflex sensitivity and pain experience in normotensive individuals", International Journal of Psychophysiology 65, (2007), 193-200.

(56) References Cited

OTHER PUBLICATIONS

Eisenberg, Elon, et al., "Quantitative Sensory Testing for Spinal Cord Stimulation in Patients With Chronic Neuropathic Pain", (2006), 161-165.
Elgendi, Mohamed, "On the analysis of fingertip photoplethysmogram signals", Current cardiology reviews 8.1, (2012), 14-25.
Evans, Subhadr, et al., "Heart rate variability as a biomarker for autonomic nervous system response differences between children with chronic pain and healthy control children", Journal of Pain Research 3.6, (2013), 449-457.
Fagius, J., et al., "The cold pressor test: effects on sympathetic nerve activity in human muscle and skin nerve fascicles", Acta physiologica Scandinavica 137.3, (1989), 325-334.
Fazalbhoy, Azharuddin, et al., "Individual differences in the cardiovascular responses to tonic muscle pain: parallel increases or decreases in muscle sympathetic nerve activity, blood pressure and heart rate", Exp Physiol 97.10, (2012), 1084-1092.
Frederiks, Joost, et al., "Within-subject electrocardiographic differences at equal heart rates: role of the autonomic nervous system", Pflügers Archiv 441.5, (2001), 717-724.
Geisser, Michael E., et al., "Pain-Related Fear, Lumbar Flexion, and Dynamic EMG Among Persons With Chronic Musculoskeletal Low Back Pain", Clin J Pain, vol. 20, No. 2, (Apr. 2004).
Generaal, Ellen, et al., "Reduced hypothalamic-pituitary-adrenal axis activity in chronic multi-site musculoskeletal pain: partly masked by depressive and anxiety disorders", BMC Musculoskeletal Disorders, 15:227, (2014), 1-11.
Gesche, Heiko, et al., "Continuous blood pressure measurement by using the pulse transit time: comparison to a cuff-based method", European journal of applied physiology 112.1, (2012), 309-315.
Godfrey, A., et al., "Direct measurement of human movement by accelerometry", Medical Engineering & Physics 30 (2008) 1364-1386.
Godfrey, A., et al., "Instrumenting gait with an accelerometer: a system and algorithm examination", Medical Engineering & Physics, Mar. 2015, doi:10.1016/j.medengphy.2015.02.003, 24 pgs.
Gouveia, S., et al., "Assessing Baroreflex Sensitivity in the Sequences Technique: Local versus Global Approach", Computers in Cardiology, 32, (2005), 279-282.
Granovsky, Yelena, et al., "Objective Correlate of Subjective Pain Perception by Contact Heat-Evoked Potentials", The Journal of Pain, vol. 9, No. 1, (Jan. 2008), 53-63.
Green, Alexande L., "Measurement of muscle sympathetic nerve activity reveals true sympathetic changes in chronic pain", Exp Physiol 97.10, (2012), 1083.
Hallman, David, et al., "Autonomic regulation, physical activity and perceived stress in subjects with musculoskeletal pain: 24-hour ambulatory monitoring", International Journal of Psychophysiology 86, (2012), 276-282.
Hallman, David M., et al., "Changes in physical activity and heart rate variability in chronic neck-shoulder pain: monitoring during work and leisure time", Int Arch Occup Environ Health 87, (2014), 735-744.
Hallman, David M., et al., "Long-Term Monitoring of Physical Behavior Reveals Different Cardiac Responses to Physical Activity among Subjects with and without Chronic Neck Pain", BioMed Research International, vol. 2015, Article ID 907482, 11 pages, http://dx.doi.org/10.1155/2015/907482, 11 pages.
Hartwich, Doreen, et al., "Effect of muscle metaboreflex activation on spontaneous cardiac baroreflex sensitivity during exercise in humans", J Physiol 589.24, (2011), 6157-6171.
Jensen, MP, et al., "Brain EEG activity correlates of chronic pain in persons with spinal cord injury: clinical implications", Nature; Spinal Cord; 51, (Jul. 17, 2012), 55-58.
Jess, Gunnar, et al., "Monitoring heart rate variability to assess experimentally induced pain using the analgesia nociception index—A randomised volunteer study", Eur J Anaesthesiol 32, (2015), 1-8.
Kang, Jon-Eun, et al., "Pulse transit time shows vascular changes caused by propofol in children", J Clin Monit Comput 29, (2015), 533-537.

Keefe, Francis J,, et al., "An Objective Approach to Quantifing Pain Behavior and Gait Patterns in Low Back Pain Patients", Pain, 21, (1985), 153-161.
Kemler, Marius A., et al., "Impact of Spinal Cord Stimulation on Sensory Characteristics in Complex Regional Pain Syndrome Type 1—A Randomized Trial", Anesthesiology, 95, (2001), 72-80.
Keshari, Kayvan R., et al., "Lactic Acid and Proteoglycans as Metabolic Markers dor Discogenic Back Pain", SPINE, vol. 13, No. 3, (2008), 312-317.
Kim, Young UK, et al., "Pulse Transit Time as a Predictor of the Efficacy of a Celiac Plexus Block in Patients With Chronic Intractable Abdominal Pain", Clin J Pain, vol. 32, No. 6, (Jun. 2015), 522-526.
Kodituwakku, Sandun, et al., "Point Process Respiratory Sinus Arrhythmia Analysis during Deep Tissue Pain Stimulation", Computing in Cardiology 38, (2011), 193-196.
Koenig, J., et al., "Heart rate variability and experimentally induced pain in healthy adults: A systematic review", European Journal of Pain 18, (2014), 301-314.
Koenig, Julian, et al., "Chronic Pain and Heart Rate Variability in a Cross-Sectional Occupational Sample Evidence for Impaired Vagal Control", The Clinical Journal of Pain, Publish Ahead of Print, (2015), 31 pgs.
La Rovere, Maria Teresa, et al., "Baroreflex Sensitivity: Measurement and Clinical Implications", Ann Noninvasive Electrodardiol, 13(2):191-207, 2008.
Lamoth, Claudine J.C., et al., "How do persons with chronic low back pain speed up and slow down? Trunk-pelvis coordination and erector spinae activity during gait", Gait & Posture 23, (2006), 230-239.
Lamoth, Claudine J.C., et al., "Pelvis-Thorax Coordination in the Transverse Plane During Walking in Persons With Nonspecific Low Back Pain", SPINE, vol. 27, No. 4, (2002), E92-E99.
Lane, James D., et al., "Respiratory Sinus Arrhythmia and Cardiovascular Responses to Stress", Psychophysiology, vol. 29, No. 4, (1992), 461-470.
Latremoliere, Alban, et al., "Reduction of Neuropathic and Inflammatory Pain through Inhibition of the Tetrahydrobiopterin Pathway", Neuron, 86 (6), (2015), 1393-1406.
Ledowski, Thomas, et al., "The influence of age and sex on the relationship between heart rate variability, haemodynamic variables and subjective measures of acute post-operative pain", European Journal of Anaesthesiology, vol. 28, No. 6, (2011), 433-437.
Lee, Jihyoung, et al., "Validation of normalized pulse volume in the outer ear as a simple measure of sympathetic activity using warm and cold pressor tests: towards applications in ambulatory monitoring", Physiol. Meas. 34, (2013), 359-375.
Lidberg, Lars, et al., "Sympathetic Skin Nerve Dischai gcs in Relation lo Anipliliule of Skin Resistance Responses", Psychophysiology, vol. 18, No. 3, (May 1981), 268-270.
Littlewort, Gwen C., et al., "Automatic Coding of Facial Expressions Displayed During Posed and Genuine Pain", Image and Vision Computing, 27(12) p. 1741-1844.
Logier, R., et al., "PhysioDoloris: a monitoring device for Analgesia / Nociception balance evaluation using Heart Rate Variability analysis", 32nd Annual International Conference of the IEEE EMBS, (2010), 1194-1197.
Looney, David, et al., "The In-the-Ear Recording Concept", IEEE Pulse Nov./Dec. 2012, 32-42.
Marchi, Antonio, et al., "Pain Biomarkers", Clin Drug Invest, 29 Suppl 1, (2009), 41-46.
Martini, Chris H., et al., "Ability of the Nociception Level, a Multiparameter Composite of Autonomic Signals, to Detect Noxious Stimuli during Propofol-Remifentanil Anesthesia", Anesthesiology, vol. 123, No. 3, (2015), 524-534.
Mauer, C,, et al., "Quantitative sensory testing in the German Research Network on Neuropathic Pain (DFNS): Somatosensory abnormalities in 1236 patients with different neuropathic pain syndromes", Pain 150, (2010), 439-450.
McBeth, John, et al., "Hypothalamic-pituitary-adrenal stress axis function and the relationship with chronic widespread pain and its antecedents", [Online]. Retrieved from the Internet: <URL: http://arthritis-research.com/content/7/5/R992, (2005), R992-R1000.

(56) References Cited

OTHER PUBLICATIONS

McCarthy, K. F., et al., "Cerebrospinal fluid levels of glial cell-derived neurotrophic factor correlate with spinal cord stimulation frequency in patients with neuropathic pain: a preliminary report", Spinal Cord 52, (2014), S8-S10.

McCracken, Lance M., et al., "Disrupted sleep patterns and daily functioning in patients with chronic pain", Pain Res Manage vol. 7 No. 2 Summer 2002 75-79.

Mikkelsen, Kaare B., et al., "EEGRecordedfromtheEar:Characteri zingtheEar—EEGMethod", FrontiersinNeuroscience|www.frontiersin. org, Nov. 2015|vol. 9|Article438, 8 pgs.

Mironer, Y. Eugene, et al., "Pain Tolerance Threshold: A Pilot Study of an Objective Measurement of Spinal Cord Stimulator Trial Results", Pain Medicine, vol. 1, No. 2, (2000), 110-115.

Moseley, G. Lorimer, et al., "Tactile Discrimination, but not tactile stimulation alone, reduces chronic limg pain", Pain 137, (2008), 600-608.

Moxham, I.M., "Understanding Arterial Pressure Waveforms", Southern African Journal of Anaesthesia and Analgesia 9.1, (2003), 40-42.

Mukkamala, R., et al., "Toward ubiquitous blood pressure monitoring via pulse transit time: theory and practice", IEEE Transactions on Biomedical Engineering 62.8, (2015), 1879-1901.

Mylius, Vett, et al., "Sex differences in nociceptive withdrawal reflex and pain perception", Somatosensory and Motor Research 22 (3), (Sep. 2005), 207-211.

Neblett, Randy, et al., "What is the Best Surface EMG Measure of Lumbar Flexion-Relation for Distinguishing Chronic Low Back Pain Patients From Pain-Free Controls?", Clin J Pain 29 (4)—NIH Public Access, (Apr. 2013), 334-340.

Ng, Joseph, et al., "EMG activity of trunk muscles and torque output during isometric axial rotation exertion: a comparison between back pain patients and matched controls", Journal of Orthopaedic Research; 20, (2002), 112-121.

Palermo, Tonya M., et al., "Subjective Sleep Disturbances in Adolescents With Chronic Pain: Relationship to Daily Functioning and Quality of Life", The Journal of Pain, vol. 6, No. 3, (Mar. 2995), 201-207.

Panjabi, Manohar, "Clinical spinal instability and low back pain", Journal of Electromyography and Kinesiology 13, (2003), 371-379.

Patti, Gary J., et al., "Metabolomics implicates altered sphingolipids in chronic pain of neuropathic origin", nature chemical biology, vol. 8, (Mar. 2012), 232-234.

Perruchoud, Christophe, et al., "Assessment of Physical Activity of Patients with Chronic Pain", Neuromodulation: Technology at the Neural Interface; 17, (2012), 42-47.

Pinheiro, Eulália Silva Dos Santos, et al., "Electroencephalographic Patterns in Chronic Pain: A Systematic Review of the Literature", PLOS ONE | DOI:10.1371/journal.pone.0149085 Feb. 25, 2016, 27 pgs.

Plaza-Manzano, Gustavo, et al., "Changes in Biochemical Markers of Pain Perception and Stress Response After Spinal Manipulation", Journal of Orthopaedic & Sports Physical Therapy, vol. 44, No. 4, (Apr. 2014), 231-239.

Pleger, Burkhard, et al., "Patterns of cortical reorginization parallel impaired tactile discrimination and pain intensity in complex regional pain syndrome", NeuroImage 32, (2006), 503-510.

Pluijms, Wouter A., et al., "Increased Contact Heat Evoked Potential Stimulation Latencies in Responders to Spinal Cord Stimulation for Painful Diabetic Cord Stimulation for Painful Diabetic Cord Stimulation for Painful Diabetic Polyneuropathy", Neuromodulation 18, (2015), 126-132.

Poon, C.C.Y., "Cuff-less and noninvasive measurements of arterial blood pressure by pulse transit time", 2005 IEEE Engineering in Medicine and Biology 27th Annual Conference. IEEE, 2006., (2006), 5877-5880.

Prichep, Leslie S., et al., "Evaluation of the Pain Matrix Using EEG Source Localization: A Feasibility Study", Pain Medicine 12, (2011), 1241-1248.

Prkachin, Kenneth, "The consistency of facial expressions of pain: a comparison across modalities", Pain, 51, (1992), 279-306.

Raminen, Tina, et al., "The Impact of Spinal Cord Stimulation on Sleep Patterns", Neuromodulation 19, (2016), 477-481.

Rasche, Dirk, et al., "Quantitative Sensory Testing in Patients With Chronic Unilateral Radicular Neuropathic Pain and Active Spinal Cord Stimulation", Neuromodulation, vol. 9, No. 3, (2006), 239-247.

Rhudy, Jamie L., et al., "Defining the nociceptive flexion reflex (NFR) threshold in human participants: A comparison of different scoring criteria", Pain 128, (2007), 244-253.

Roy, Sourav Dey, et al., "An Approach for Automatic Pain Detection through Facial Expression", Procedia Computer Science 84 (2016) 99-106.

Sacco, Marcella, et al., "The Relationship Between Blood Pressure and Pain", The Journal of Clinical Hypertension vol. 15, No. 8, (Aug. 2013), 600-605.

Sarnthein, Johannes, et al., "Increased EEG power and slowed dominant frequncy in patients with neurogenic pain", Brain 129, (2005), 55-64.

Sato, Karina L/, et al., "Spinal Cord Stimulation (SCS) Improves Decreased Physical Activity Induced by Nerve Injury", Behavioral Neuroscience, vol. 128, No. 5, (2914), 625-632.

Sawada, Yukihiro, et al., "Normalized pulse volume (NPV) derived photo-plethysmography as a more valid measure of the finger vascular tone", International Journal of Psychophysiology 41, (2001), 1-10.

Sayar, Kemal, et al., "Sleep Quality in Chronic Pain Patients", Can J. Psychiatry, vol. 47, No. 9, (Nov. 2002), 844-848.

Schulman, Joshua J., et al., "Thalamocortical dysrhythmia syndrome: MEG imaging of neuropathic pain", (Jul. 25, 2014), 33-39.

Schulz, Enrico, et al., "Prefrontal Gamma Oscillations Encode Tonic Pain in Humans", Cerebral Cortex 2015, (Mar. 8, 2015), 1-8.

Sesay, Musa, et al., "Responses of Heart Rate Variability to Acute Pain After Minor Spinal Surgery: Optimal Thresholds and Correlation With the Numeric Rating Scale", J Neurosurg Anesthesiol, vol. 00, No. 00, (2014), 1-7.

Shouldice, R., "PR and PP ECG intervals as indicators of autonomic nervous innervation of the cardiac sinoatrial and atrioventricular nodes", Neural Engineering, 2003. Conference Proceedings. First International IEEE EMBS Conference on. IEEE, (Mar. 2003), 261-264.

Siddall, Phillip J., et al., "Magnetic Resonance Spectroscopy Detects Biochemical Changes in the Brain Associated with Chronic Low Back Pain: A Preliminary Report", Anesth Analg 102, (2006), 1164-1168.

Sihvonen, T., et al., "Electric behavior of low back muscles during lumbar pelvic rhythm in low back pain patients and healthy controls", Archives of physical medicine and rehabilitation; 72.13, (1991), 1080-1087.

Simoes, Mario A., "Feasibility of Wearable Sensors to Determine Gait Parameters", University of South Florida Scholar Commons, (2011), 1-98.

Skljarevski, V., et al., "The nociceptive flexion reflex in humans— review article", Pain, 96, (2002), 3-8.

Smallwood, Rachel F., et al., "Structural Brain Anomalies and Chronic Pain: A Quantitative Meta-Analysis of Gray Matter Volume", The Journal of Pain, vol. 14, No. 7, (Jul. 2013), 663-675.

Srivastava, Kyle Harish, et al., "Pain Management Based on Cardiovascular Parameters", U.S. Appl. No. 62/445,053, filed Jan. 11, 2017.

Srivastava, Kyle Harish, et al., "Pain Management Based on Emotional Expression Measurements", U.S. Appl. No. 62/445,082, filed Jan. 11, 2017.

Staud, Roland, "Heart rate variability as a biomarker of fibromyalgia syndrome", Fut Rheumatol 3 (5)—NIH Public Access, (Oct. 1, 2008), 475-483.

Storm, H., et al., "Skin conductance correlates with perioperative stress", Acta Anaesthesiol Scand 46, (2002), 887-895.

Sturgeon, John A., et al., "Respiratory Sinus Arrhythmia: a Marker of Resilience to Pain Induction", Int.J. Behay. Med. 21, (2014), 961-965.

(56) References Cited

OTHER PUBLICATIONS

Swenne, C. A., "Baroreflex sensitivity: mechanisms and measurement", Neth Heart J 21, (2013), 58-60.
Symons, Frank J., et al., "Can Biomarkers Differentiate Pain and No Pain Subgroups of Nonverbal Children with Cerebral Palsy? A Preliminary Investigation Based on Noninvasive Saliva Sampling", Pain Med 16 (2), (2015), 249-256.
Tagliazucchi, Enzo, et al., "Brain resting state is disrupted in chronic back pain patients", Neurosci Lett. 485 (1)—NIH Public Access, (Nov. 12, 2010), 26-31.
Tao, Weijun, et al., "Gait Analysis Using Wearable Sensors", Sensors 12, (2012), 2255-2283.
Tauda, Makoto, et al., "P2X4receptorsandneuropathicpain", Frontiers in Cellular Neuroscience, vol. 7, Article 191, (Oct. 28, 2013), 1-6.
Terkelsen, Astrid J., et al., "Heart Rate Variability in Complex Regional Pain Syndrome during Rest and Mental and Orthostatic Stress", Anesthesiology, vol. 116, No. 1, (Jan. 2012), 133-146.
Thakur, Pramodsingh Hirasingh, et al., "Method and Apparatus for Pain Control Using Baroreflex Sensitivity During Posture Change", U.S. Appl. No. 62/412,587, filed Oct. 25, 2016.
Thakur, Pramodsingh Hirasingh, et al., "Systems and Methods for Closed-Loop Pain Management", U.S. Appl. No. 62/400,313, filed Sep. 27, 2016.
Thankur, Pramodsingh Hirasingh, et al., "Method and Apparatus for Pain Management Using Heart Sounds", U.S. Appl. No. 62/395,641, filed Sep. 16, 2016.
Theuvenel, Peter J., et al., "Responses to Median and Tbial Nerve Stimulation in Patients with Chronic Neuropathic Pain", Brain Topography, vol. 11, No. 4, (1999), 306-313.
Uceyler, Nuncan, et al., "Differential expression of cytokines in painful and painless neuropathies", (2007).
Uzar, E., et al., "Serum cytokine and pro-brain natriuretic peptide (BNP) levels in patients with migraine", European Review for Medical and Pharmacological Sciences; 15, (2011), 1111-1116.
Van Velzen, Marit H.N., et al., "Effect of heat-induced pain stimuli on pulse transit time and pulse wave amplitude in healthy volunteers", Physiological Measurement 37, (2016), 52-66.
Villarejo, Viqueira Maria, et al., "A Stress Sensor Based on Galvanic Skin Response (GSR) Controlled by ZigBee", Sensors 12, (2012), 6075-6101.
Walton, K. D., et al., "Abnormal thalamocortical activity in patients with Complex Regional Pain Syndrome (CRPS) Type 1", Pain 150, (2010), 41-51.
Willer, Jean Claude, "Comparative Study of Perceived Pain and Nociceptive Flexion Reflex in Man", Pain, 3, (1977), 69-80.
Williams, Dewayne P., et al., "Effects of Chronic Pelvic Pain on Heart Rate Variability in Women", The Journal of Urology, vol. 194,, (Nov. 2015), 1-6.
Wong, Arnold Y.L., et al., "Does experimental low back pain change posteroanterior lumbar spinal stiffness and trunk muscle activity? A randomized crossover study", Clinical Biomechanics 34, (2016), 45-52.
Wong, Jih-Sen, et al., "A comparative study of pulse rate variability and heart rate variability in healthy subjects", J Clin Monit Comput 26, (2012), 107-114.
Wu, Hao-Yu, et al., "Eulerian Video Magnification for Revealing Subtle Changes in the World", ACM Transactions on Graphics 31, No. 4, (Jul. 1, 2012), 1-8.
Zamuner, Antonio R., et al., "Respiratory Sinus Arrhythmia and its Association with Pain in Women with Fibromyalgia Syndrome", Pain Practice, vol. 16, Issue 6, (2016), 704-711.
Zamunér, A. R., et al., "Relationship between sympathetic activity and pain intensity in fibromyalgia", Clin Exp Rheumatol 33—Abstract, [Online]. Retrieved from the Internet: <URL: http://www.ncbi.nlm.nih.gov.ezp3.lib.umn.edu/pubmed/25786044, (Feb. 2015), 1-2.
Zeng, Zhihong, et al., "A Survey of Affect Recognition Methods: Audio, Visual and Spontaneous Expressions", ICMI'07, Nov. 12-15, 2007, 126-133.

Zhang, John, "Effect of Chiropractic Care on Heart Rate Variability and Pain in a Multisite Clinical Study", Jimmal of Manipulative and Physiological Therapeutics, vol. 29, No. 4, (2006), 267-274.
Zhou, Jing, et al., "Recurrent Convolutional Neural Network Regression for Continuous Pain Intensity Estimation in Video", arXiv preprint arXiv:1605.00894 (2016) 84-92.
Zhou, Jing, et al., "Recurrent Convolutional Neural Network Regression for Continuous Pain Intensity Estimation in Video", Technical Report, (May 3, 2016), 1-11.
"U.S. Appl. No. 15/687,925, Final Office Action dated Feb. 14, 2019", 10 pgs.
"U.S. Appl. No. 15/687,925, Non Final Office Action dated Jun. 11, 2019", 11 pgs.
"U.S. Appl. No. 15/687,925, Non Final Office Action dated Oct. 9, 2018", 9 pgs.
"U.S. Appl. No. 15/687,925, Response filed Jan. 9, 2019 to Non Final Office Action dated Oct. 9, 2018", 9 pgs.
"U.S. Appl. No. 15/687,925, Response filed May 13, 2019 to Final Office Action dated Feb. 14, 2019", 11 pgs.
"U.S. Appl. No. 15/688,676, Examiner Interview Summary dated Sep. 25, 2019", 3 pgs.
"U.S. Appl. No. 15/688,676, Final Office Action dated Jul. 29, 2019", 7 pgs.
"U.S. Appl. No. 15/688,676, Non Final Office Action dated Jan. 11, 2019", 7 pgs.
"U.S. Appl. No. 15/688,676, Non Final Office Action dated Oct. 30, 2019", 6 pgs.
"U.S. Appl. No. 15/688,676, Response filed Sep. 25, 2019 to Final Office Action dated Jul. 29, 2019", 10 pgs.
"U.S. Appl. No. 15/688,676, Response filed Apr. 9, 2019 to Non Final Office Action dated Jan. 11, 2019", 12 pgs.
"U.S. Appl. No. 15/711,578, Examiner Interview Summary dated Aug. 28, 2019", 3 pgs.
"U.S. Appl. No. 15/711,578, Non Final Office Action dated May 23, 2019", 6 pgs.
"U.S. Appl. No. 15/711,578, Notice of Allowance dated Nov. 25, 2019", 7 pgs.
"U.S. Appl. No. 15/711,578, Repsonse filed Aug. 23, 2019 to Non Final Office Action dated May 23, 2019", 11 pgs.
"U.S. Appl. No. 15/711,578, Supplemental Response filed Aug. 28, 2019 to Non Final Office Action dated May 23, 2019", 11 pgs.
"U.S. Appl. No. 15/788,403, Non Final Office Action dated Jul. 23, 2019", 9 pgs.
"U.S. Appl. No. 15/788,403, Response filed Oct. 8, 2019 to Non Final Office Action dated Jul. 23, 2019", 11 pgs.
"U.S. Appl. No. 15/867,756, Examiner Interview Summary dated Aug. 28, 2019", 3 pgs.
"U.S. Appl. No. 15/867,756, Non Final Office Action dated Jul. 1, 2019", 8 pgs.
"U.S. Appl. No. 15/867,756, Response filed Aug. 29, 2019 to Non Final Office Action dated Jul. 1, 2019", 11 pgs.
"U.S. Appl. No. 15/867,760, Examiner Interview Summary dated Aug. 28, 2019", 3 pgs.
"U.S. Appl. No. 15/867,760, Non Final Office Action dated Jul. 1, 2019", 8 pgs.
"U.S. Appl. No. 15/867,760, Response filed Aug. 29, 2019 to Non-Final Office Action dated Jul. 1, 2019", 11 pgs.
"U.S. Appl. No. 15/867,767, Non Final Office Action dated Dec. 17, 2019", 11 pgs.
"U.S. Appl. No. 15/888,808, Examiner Interview Summary dated Nov. 21, 2019", 3 pgs.
"U.S. Appl. No. 15/888,808, Final Office Action dated Dec. 16, 2019", 7 pgs.
"U.S. Appl. No. 15/888,808, Non Final Office Action dated Sep. 11, 2019", 7 pgs.
"U.S. Appl. No. 15/888,808, Response filed Nov. 19, 2019 to Non Final Office Action dated Sep. 11, 2019", 10 pgs.
"Australian Application Serial No. 2017325823, First Examination Report dated Jun. 19, 2019", 3 pgs.
"Australian Application Serial No. 2017334841, First Examination Report dated Jun. 24, 2019", 3 pgs.
"Australian Application Serial No. 2017335497, First Examination Report dated Jun. 26, 2019", 3 pgs.

(56) References Cited

OTHER PUBLICATIONS

"Australian Application Serial No. 2017335497, Response filed Nov. 27, 2019 to First Examination Report dated Jun. 26, 2019", 18 pgs.
"European Application Serial No. 17762308.9, Response to Communication pursuant to Rules 161 & 162 dated Nov. 26, 2019", 23 pgs.
"International Application Serial No. PCT/US2017/048867, International Preliminary Report on Patentability dated Mar. 28, 2019", 8 pgs.
"International Application Serial No. PCT/US2017/048896, International Preliminary Report on Patentability dated Apr. 11, 2019", 8 pgs.
"International Application Serial No. PCT/US2017/052685, International Preliminary Report on Patentability dated Apr. 11, 2019", 6 pgs.
"International Application Serial No. PCT/US2017/057367, International Preliminary Report on Patentability dated May 9, 2019", 6 pgs.
"International Application Serial No. PCT/US2017/057367, International Search Report dated Jan. 19, 2018", 4 pgs.
"International Application Serial No. PCT/US2017/057367, Written Opinion dated Jan. 19, 2018", 4 pgs.
"International Application Serial No. PCT/US2018/013251, International Preliminary Report on Patentability dated Jul. 25, 2019", 7 pgs.
"International Application Serial No. PCT/US2018/013251, International Search Report dated Apr. 12, 2018", 4 pgs.
"International Application Serial No. PCT/US2018/013251, Written Opinion dated Apr. 12, 2018", 5 pgs.
"International Application Serial No. PCT/US2018/013257, International Preliminary Report on Patentability dated Jul. 25, 2019", 8 pgs.
"International Application Serial No. PCT/US2018/013257, International Search Report dated Apr. 19, 2018", 4 pgs.
"International Application Serial No. PCT/US2018/013257, Written Opinion dated Apr. 19, 2018", 6 pgs.
"International Application Serial No. PCT/US2018/013268, International Preliminary Report on Patentability dated Jul. 25, 2019", 13 pgs.
"International Application Serial No. PCT/US2018/013268, International Search Report dated Apr. 30, 2018", 5 pgs.
"International Application Serial No. PCT/US2018/013268, Written Opinion dated Apr. 30, 2018", 11 pgs.
Ashraf, A B, et al., "The painful face—Pain expression recognition using active appearance models", Image and Vision Computing Elsevier Guildford, GB, vol. 27, No. 12, (Nov. 1, 2009), 1788-1796.
Berthomier, Christian, et al., "Automatic analysis of single-channel sleep EEG: validation in healthy individuals", Sleep—New York Then Westchester—30.11, 2007, 1587-1595.
Bunde, Armin, et al., "Correlated and uncorrelated regions in heart-rate fluctuations during sleep", Physical Review Letters 85.17, (2000), 3736-3739.
Foo, H., et al., "Brainstem modulation of pain during sleep and waking", Sleep medicine reviews 7.2, (2003), 145-154.
Sano, Akane, et al., "Quantitative analysis of wrist electrodermal activity during sleep", Int J Psychophysiol. Dec. 2014 ; 94(3), (2014), 382-389.
Sotocinal, S G, et al., "The Rat Grimace Scale partially automated method for quantifying pain in the laboratory rat via facial expressions", Molecular Pain Biomed Central, London, GB, vol. 7 No. 1, (Jul. 29, 2011), 1744-8069.

\* cited by examiner

PAIN MANAGEMENT BASED ON BRAIN ACTIVITY MONITORING

CROSS REFERENCE TO RELATED APPLICATIONS

This application claims the benefit of priority under 35 U.S.C. § 119(e) of U.S. Provisional Patent Application Ser. No. 62/445,061, filed on Jan. 11, 2017, which is herein incorporated by reference in its entirety.

CROSS REFERENCE TO RELATED APPLICATIONS

This application is related to commonly assigned U.S. Provisional Patent Application Ser. No. 62/445,053, entitled "PAIN MANAGEMENT USING CARDIOVASCULAR PARAMETERS", filed on Jan. 11, 2017, U.S. Provisional Patent Application Ser. No. 62/445,069, entitled "PAIN MANAGEMENT BASED ON RESPIRATION-MEDIATED HEART RATES", filed on Jan. 11, 2017, U.S. Provisional Patent Application Ser. No. 62/445,075, entitled "PAIN MANAGEMENT BASED ON FUNCTIONAL MEASUREMENTS", filed on Jan. 11, 2017, U.S. Provisional Patent Application Ser. No. 62/445,082, entitled "PAIN MANAGEMENT BASED ON EMOTIONAL EXPRESSION MEASUREMENTS", filed on Jan. 11, 2017, U.S. Provisional Patent Application Ser. No. 62/445,092, entitled "PAIN MANAGEMENT BASED ON MUSCLE TENSION MEASUREMENTS", filed on Jan. 11, 2017, U.S. Provisional Patent Application Ser. No. 62/445,095, entitled "PATIENT-SPECIFIC CALIBRATION OF PAIN QUANTIFICATION", filed on Jan. 11, 2017, U.S. Provisional Patent Application Ser. No. 62/395,641, entitled "METHOD AND APPARATUS FOR PAIN MANAGEMENT USING HEART SOUNDS", filed on Sep. 16, 2016, U.S. Provisional Patent Application Ser. No. 62/400,313, entitled "SYSTEMS AND METHODS FOR CLOSED-LOOP PAIN MANAGEMENT", filed on Sep. 27, 2016, U.S. Provisional Patent Application Ser. No. 62/400,336, entitled "METHOD AND APPARATUS FOR PAIN MANAGEMENT USING OBJECTIVE PAIN MEASURE", filed on Sep. 27, 2016, U.S. Provisional Patent Application Ser. No. 62/412,587, entitled "METHOD AND APPARATUS FOR PAIN CONTROL USING BAROREFLEX SENSITIVITY DURING POSTURE CHANGE", filed on Oct. 25, 2016, which are incorporated by reference in their entirety.

TECHNICAL FIELD

This document relates generally to medical systems and more particularly to systems, devices, and methods for pain management.

BACKGROUND

Pain is one of the most common and among the most personally compelling reasons for seeking medical attention, and consumes considerable healthcare resources each year. The relation between etiology, underlying mechanisms and the specific symptoms and signs related to painful disorders is complex. Pain in an individual patient may be produced by more than one mechanism.

Chronic pain, such as pain present most of the time for a period of six months or longer during the prior year, is a highly pervasive complaint and consistently associated with psychological illness. Chronic pain may originate with a trauma, injury or infection, or there may be an ongoing cause of pain. Chronic pain may also present in the absence of any past injury or evidence of body damage. Common chronic pain can include headache, low back pain, cancer pain, arthritis pain, neurogenic pain (pain resulting from damage to the peripheral nerves or to the central nervous system), or psychogenic pain (pain not due to past disease or injury or any visible sign of damage inside or outside the nervous system).

Chronic pain may be treated or alleviated using medications, acupuncture, surgery, and neuromodulation therapy such as local electrical stimulation or brain stimulation, among others. Examples of neuromodulation include Spinal Cord Stimulation (SCS), Deep Brain Stimulation (DBS), Peripheral Nerve Stimulation (PNS), and Functional Electrical Stimulation (FES). Implantable neuromodulation systems have been applied to deliver such a therapy. An implantable neuromodulation system may include an implantable neurostimulator, also referred to as an implantable pulse generator (IPG), which can electrically stimulate tissue or nerve centers to treat nervous or muscular disorders. In an example, an IPG can deliver electrical pulses to a specific region in a patient spinal cord, such as particular spinal nerve roots or nerve bundles, to create an analgesic effect that masks pain sensation.

SUMMARY

By way of example, chronic pain management may involve determining appropriate treatment regimens such as SCS and evaluating therapy efficacy. Accurate pain assessment and characterization are desirable for managing patients with chronic pain. Currently, pain assessment generally relies on patient subjective report of pain symptoms, including severity, pattern, or duration of pain. Based on the patient reported pain sensation, a clinician may prescribe a pain therapy, such as to manually program an electrostimulator for delivering a neuromodulation therapy. However, the subjective description of pain sensation may be constrained by patient cognitive abilities. The subjective pain description may also be subject to intra-patient variation, such as due to a progression of a chronic disease, or a change in general health status or medication. Having a patient to report and describe each pain episode he or she has experienced is not efficient and may delay appropriate pain therapy. Additionally, for patients in an ambulatory setting who lack immediate access to medical assistance, manual adjustment of pain therapy by a clinician may not be feasible especially if immediate therapy titration is required. The present inventors have recognized that there remains a demand for improving pain management, such as systems and methods for objective pain assessment and automated closed-loop pain therapy based on objective pain assessment.

This document discusses, among other things, systems, devices, and methods for assessing pain of a subject. The system includes one or more physiological sensors configured to sense a physiological signal indicative of patient brain activity. The physiological signals may include an electroencephalography (EEG) signal, a magnetoencephalography (MEG) signal, or a brain-evoked potential. The system may extract from the physiological signal one or more signal metrics indicative of strength or pattern of brain electromagnetic activity associated with pain, and generate a pain score using the one or more signal metrics. The pain score can be output to a patient or used for closed-loop control of a pain therapy.

Example 1 is a system for managing pain of a patient. The system comprises a sensor circuit, a pain analyzer circuit, and an output unit. The sensor circuit may be coupled to one or more physiological sensors and configured to sense from the patient at least one physiological signal indicative of patient brain activity. The pain analyzer circuit may be coupled to the sensor circuit and configured to generate, from each of the sensed at least one physiological signal indicative of the patient brain activity, one or more signal metrics indicative of strength or a pattern of brain electromagnetic activity associated with pain, and generate a pain score using the generated one or more signal metrics. The output unit may be configured to output the pain score to a user or a process.

In Example 2, the subject matter of Example 1 optionally includes an electrostimulator configured to generate electrostimulation energy to treat pain, and a controller circuit coupled to the pain analyzer circuit and the electrostimulator. The controller circuit may be configured to control the electrostimulator to deliver a pain therapy and to control the electrostimulation energy generated by the electrostimulator according to the pain score.

In Example 3, the subject matter of Example 2 optionally includes the controller circuit that may be further configured to select, based on the pain score, one or more active electrodes from a plurality of candidate electrodes, and control the electrostimulator to deliver the pain therapy using the selected one or more active electrodes.

In Example 4, the subject matter of Example 3 optionally includes the pain analyzer circuit that may be configured to generate pain scores respectively associated with the plurality of candidate electrodes. The pain scores each may be indicative of patient pain during electrostimulation delivered using a respective candidate electrode. The selected one or more active electrodes correspond to respective pain scores less than pain scores associated with other candidate electrodes different from the selected one or more active electrodes.

In Example 5, the subject matter of any one or more of Examples 3-4 optionally includes the controller circuit that may be further configured to determine electrostimulation energy fractionalization for the one or more active electrodes based on the pain score.

In Example 6, the subject matter of any one or more of Examples 2-5 optionally includes the electrostimulator that may be further configured to deliver at least one of a spinal cord stimulation, a brain stimulation, or a peripheral nerve stimulation.

In Example 7, the subject matter of any one or more of Examples 1-6 optionally includes the at least one physiological signal that may include one or more electroencephalography (EEG) signals each recorded at a brain region of interest.

In Example 8, the subject matter of Example 7 optionally includes the one or more physiological sensors that may include one or more electrodes disposed on a lead configured to be implanted in a patient brain. The sensor circuit may be configured to sense the one or more EEG signals via the one or more electrodes disposed on the lead.

In Example 9, the subject matter of Example 8 optionally includes the one or more electrodes disposed on the lead that may be further configured to deliver electrostimulation energy to treat pain.

In Example 10, the subject matter of Example 7 optionally includes the one or more physiological sensors that may include one or more wearable sensors communicatively coupled to the sensor circuit. The one or more wearable sensors may be removably worn on a patient head, and the sensor circuit may be configured to sense the one or more EEG signals via the one or more wearable sensors.

In Example 11, the subject matter of Example 7 optionally includes the one or more signal metrics that may include EEG power spectra at one or more frequency bands.

In Example 12, the subject matter of any one or more of Examples 1-11 optionally includes the at least one physiological signal that may include a magnetoencephalography signal.

In Example 13, the subject matter of any one or more of Examples 1-12 optionally includes the at least one physiological signal that may include a brain-evoked potential.

In Example 14, the subject matter of any one or more of Examples 1-13 optionally includes the pain analyzer circuit that may be further configured to generate the pain score using a combination of a plurality of the signal metrics weighted by their respective weight factors.

In Example 15, the subject matter of Example 2 optionally includes an implantable neuromodulator device that includes one or more of the sensor circuit, the pain analyzer circuit, or the electrostimulator.

Example 16 is a method for managing pain of a patient using an implantable neuromodulator device (IND). The method comprises steps of: sensing at least one physiological signal from the patient via a sensor circuit, the at least one physiological signal indicative of patient brain activity; generating, from each of the sensed at least one physiological signal indicative of the patient brain activity, one or more signal metrics indicative of strength or a pattern of brain electromagnetic activity associated with pain; generating a pain score based on the generated one or more signal metrics; and outputting the pain score to a user or a process.

In Example 17, the subject matter of Example 16 optionally includes delivering a pain therapy via the IND, the pain therapy including electrostimulation energy determined according to the pain score.

In Example 18, the subject matter of Example 17 optionally includes selecting, based on the pain score, one or more active electrodes from a plurality of candidate electrodes, and delivering the pain therapy using the selected one or more active electrodes.

In Example 19, the subject matter of Example 18 optionally includes selecting one or more active electrodes that may include steps of: generating pain scores respectively associated with the plurality of candidate electrodes, the pain scores each indicative of patient pain during electrostimulation delivered using a respective candidate electrode; and selecting one or more active electrodes with respective pain scores less than pain scores associated with other candidate electrodes different from the selected one or more active electrodes.

In Example 20, the subject matter of Example 18 optionally includes determining electrostimulation energy fractionalization for the one or more active electrodes based on the pain score.

In Example 21, the subject matter of Example 16 optionally includes the at least one physiological signal that may include one or more electroencephalography (EEG) signals each recorded at a brain region of interest via an implantable or wearable sensor.

In Example 22, the subject matter of Example 21 optionally includes sensing the one or more EEG signals via one or more electrodes disposed on a lead implanted in a patient brain, and delivering electrostimulation energy to treat pain via the one or more electrodes disposed on the lead.

In Example 23, the subject matter of Example 16 optionally includes generating the pain score that may include using a combination of a plurality of the signal metrics weighted by their respective weight factors.

Objective pain assessment based on pain scores generated from information about patient brain activity, such as brain electromagnetic signals as discussed in this document, may improve automated patient pain characterization, as well as individualized therapies to alleviate pain or to reduce side effects. The systems, devices, and methods discussed in this document may also enhance the performance and functionality of a pain management system or device. A device or a system programmed with the brain activity-based pain assessment methods can lead to improved automaticity in medical diagnostics. More efficient device memory or communication bandwidth usage may be achieved by storing or transmitting medical information more relevant to clinical decisions. Additionally, through improved pain therapy efficacy based on patient individual need, battery longevity of an implantable device may be enhanced, or pain medication volume may be saved.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
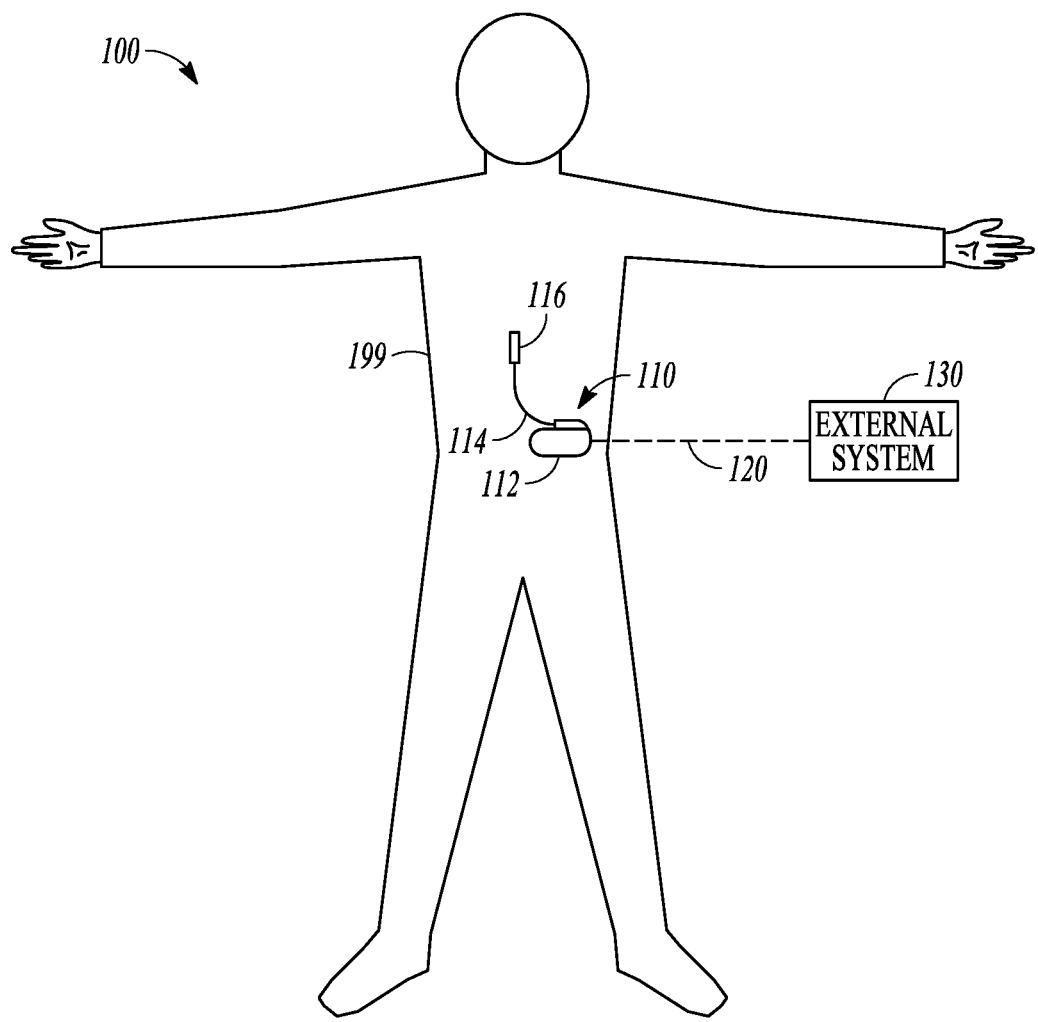
FIG. 1 illustrates, by way of example and not limitation, a neuromodulation system and portions of an environment in which the neuromodulation system may operate.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

Clinically, electroencephalography (EEG) and magnetoencephalography (MEG) studies are used to evaluate separate temporal and spatial components of the cerebral pain response. In clinical contexts, EEG refers to the recording of the brain's spontaneous electrical activity over a period of time and at distinctive scalp locations. EEG measures voltage fluctuations resulting from ionic current within the neurons of the brain, and can be recorded from multiple electrodes placed on the scalp. Certain EEG patterns may be associated with patient vulnerability to experience chronic pain in persons with spinal cord injury. Chronic neuropathic pain may also be associated with changes in EEG characteristics, including increased power density and peak frequency in the low frequency ranges. The ionic currents occurring naturally in the brain that produce the EEG signal also generate magnetic field, which can be measured as MEG. MEG is a functional neuroimaging technique for mapping brain activity by recording magnetic fields. It provides timing as well as spatial information about brain activity. Evoked potential is an electrical potential recorded from the nervous system, such as a brain, following presentation of a stimulus, which may be distinct from spontaneous neural potentials. The stimulus may be delivered through sight, hearing, touch, or electrical, mechanical, or pharmacological stimulus. The evoked electrical potentials travel along nerves to the brain, and can be recorded with electrodes attached to the scalp and skin over various peripheral sensory nerves. Close monitoring of patient brain electromagnetic activity may provide an objective assessment of pain, and may be used to improve pain therapy efficacy.

Disclosed herein are systems, devices, and methods for or assessing pain of a subject, and optionally programming pain therapy based on the pain assessment. In various embodiments, the present system may include sensors configured to sense physiological signals indicative of brain electromagnetic activity, such as an EEG signal, a MEG signal, or a brain-evoked potential. A pain analyzer circuit may generate a pain score using signal metrics extracted from the brain electromagnetic activity signals. The system may include a neurostimulator that can deliver a pain therapy according to the pain score.

The present system may be implemented using a combination of hardware and software designed to provide a closed-loop pain management regimen to increase therapeutic efficacy, increase patient satisfaction for neurostimulation therapies, reduce side effects, and/or increase device longevity. The present system may be applied in any neurostimulation (neuromodulation) therapies, including but not limited to SCS, DBS, PNS, FES, motor cortex stimulation, sacral nerve stimulation, radiofrequency ablation, and vagus nerve stimulation (VNS) therapies. In various examples, instead of providing closed-loop pain therapies, the systems, devices, and methods described herein may be used to monitor the patient and assess pain that either occurs spontaneously or is induced by nerve block procedures or radiofrequency ablation therapies, or side effects like paresthesia caused by the stimulation therapy. The patient monitoring may include generating recommendations to the patient or a clinician regarding pain treatment.

FIG. 1 illustrates, by way of example and not limitation, a neuromodulation system 100 for managing pain of a subject such as a patient with chronic pain, and portions of an environment in which the neuromodulation system 100 may operate. The neuromodulation system 100 may include an implantable system 110 that may be associated with a body 199 of the subject, and an external system 130 in communication with the implantable system 110 via a communication link 120.

The implantable system 110 may include an ambulatory medical device (AMD), such as an implantable neuromodulator device (IND) 112, a lead system 114, and one or more electrodes 116. The IND 112 may be configured for subcutaneous implant in a patient's chest, abdomen, upper gluteal surface, or other parts of the body 199. The IND 112 may be configured as a monitoring and diagnostic device. The IND 112 may include a hermetically sealed can that houses sensing circuitry to sense physiological signals from the patient via sensing electrodes or ambulatory sensors associated with the patient and in communication with the IND 112, such as the one or more electrodes 116. In some examples, the sensing electrodes or the ambulatory sensors may be included within the IND 112. The physiological signals, when measured during a pain episode, may be correlative to severity of the pain. In an example, the one or more electrodes 116 may be surgically positioned on at least a portion of the brain to sense brain activity therein. The brain activity may include brain electromagnetic activity such as represented as an EEG, a MEG, or brain-evoked potentials. The IND 112 may characterize patient pain based on the sensed physiological signals, such as to determine an onset, intensity, severity, duration, or patterns of the pain experienced by the subject. The IND 112 may generate an alert to indicate the pain episode or pain exacerbation, or efficacy of a pain therapy, and present the alert to a clinician.

The IND 112 may alternatively be configured as a therapeutic device for treating or alleviating the pain. In addition to the pain monitoring circuitry, the IND 112 may further include a therapy unit that can generate and deliver energy or modulation agents to a target tissue. The energy may include electrical, magnetic, thermal, or other types of energy. In some examples, the IND 112 may include a drug delivery system such as a drug infusion pump that can deliver pain medication to the patient, such as morphine sulfate or ziconotide, among others.

The IND 112 may include electrostimulation circuitry that generates electrostimulation pulses to stimulate a neural target via the electrodes 116 operably connected to the IND 112. In an example, the electrodes 116 may be positioned on or near a spinal cord, and the electrostimulation circuitry may be configured to deliver SCS to treat pain. In another example, the electrodes 116 may be surgically placed at other neural targets such as a brain or a peripheral neutral tissue, and the electrostimulation circuitry may be configured to deliver brain or peripheral stimulations. Examples of electrostimulation may include deep brain stimulation (DBS), trigeminal nerve stimulation, occipital nerve stimulation, vagus nerve stimulation (VNS), sacral nerve stimulation, sphenopalatine ganglion stimulation, sympathetic nerve modulation, adrenal gland modulation, baroreceptor stimulation, or transcranial magnetic stimulation, spinal cord stimulation (SCS), dorsal root ganglia (DRG) stimulation, motor cortex stimulation (MCS), transcranial direct current stimulation (tDCS), transcutaneous spinal direct current stimulation (tsDCS), pudendal nerve stimulation, multifidus muscle stimulation, transcutaneous electrical nerve stimulation (TENS), tibial nerve stimulation, among other peripheral nerve or organ stimulation. The IND 112 may additionally or alternatively provide therapies such as radiofrequency ablation (RFA), pulsed radiofrequency ablation, ultrasound therapy, high-intensity focused ultrasound (HIFU), optical stimulation, optogenetic therapy, magnetic stimulation, other peripheral tissue stimulation therapies, other peripheral tissue denervation therapies, or nerve blocks or injections.

In various examples, the electrodes 116 may be distributed in one or more leads of the lead system 114 electrically coupled to the IND 112. In an example, the lead system 114 may include a directional lead that includes at least some segmented electrodes circumferentially disposed about the directional lead. Two or more segmented electrodes may be distributed along a circumference of the lead. The actual number and shape of leads and electrodes may vary according to the intended application. Detailed description of construction and method of manufacturing percutaneous stimulation leads are disclosed in U.S. Pat. No. 8,019,439, entitled "Lead Assembly and Method of Making Same," and U.S. Pat. No. 7,650,184, entitled "Cylindrical Multi-Contact Electrode Lead for Neural Stimulation and Method of Making Same," the disclosures of which are incorporated herein by reference. The electrodes 116 may provide an electrically conductive contact providing for an electrical interface between the IND 112 and tissue of the patient. The neurostimulation pulses are each delivered from the IND 112 through a set of electrodes selected from the electrodes 116. In various examples, the neurostimulation pulses may include one or more individually defined pulses, and the set of electrodes may be individually definable by the user for each of the individually defined pulses.

Although the discussion herein with regard to the neuromodulation system 100 focuses on an implantable device such as the IND 112, this is meant only by way of example and not limitation. It is within the contemplation of the present inventors and within the scope of this document, that the systems, devices, and methods discussed herein may also be used for pain management via subcutaneous medical devices, wearable medical devices (e.g., wrist watches, patches, garment- or shoe-mounted devices, headgear, eye glasses, or earplugs), or other external medical devices, or a combination of implantable, wearable, or other external devices. The therapy, such as electrostimulation or medical therapies, may be used to treat various neurological disorders other than pain, which by way of example and not limitation may include epilepsy, migraine, Tourette's syndrome, obsessive compulsive disorder, tremor, Parkinson's disease, or dystonia, among other movement and affective disorders.

The external system 130 may be communicated with the IND 112 via a communication link 120. The external system 130 may include a dedicated hardware/software system such as a programmer, a remote server-based patient management system, or alternatively a system defined predominantly by software running on a standard personal computer. In some examples, at least a portion of the external system 130 may be ambulatory such as configured to be worn or carried by a subject. The external system 130 may be configured to control the operation of the IND 112, such as to program the IND 112 for delivering neuromodulation therapy. The external system 130 may additionally receive via the communication link 120 information acquired by IND 112, such as one or more physiological signals. In an example, the external system 130 may determine a pain score based on the physiological signals received from the IND 112, and program the IND 112 to deliver pain therapy in a closed-loop fashion. Examples of the external system and neurostimulation based on pain score are discussed below, such as with reference to FIGS. 2-3.

The communication link 120 may include one or more communication channels and intermediate devices between the external system and the IND, such as a wired link, a telecommunication link such as an internet connection, or a wireless link such as one or more of an inductive telemetry link, a radio-frequency telemetry link. The communication link 120 may provide for data transmission between the IND 112 and the external system 130. The transmitted data may include, for example, real-time physiological signals acquired by and stored in the IND 112, therapy history data, data indicating device operational status of the IND 112, one or more programming instructions to the IND 112 which may include configurations for sensing physiologic signal or stimulation commands and stimulation parameters, or device self-diagnostic test, among others. In some examples, the IND 112 may be coupled to the external system 130 further via an intermediate control device, such as a handheld external remote control device to remotely instruct the IND 112 to generate electrical stimulation pulses in accordance with selected stimulation parameters produced by the external system 130, or to store the collected data into the external system 130.

Portions of the IND 112 or the external system 130 may be implemented using hardware, software, firmware, or combinations thereof. Portions of the IND 112 or the external system 130 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, or a portion thereof. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
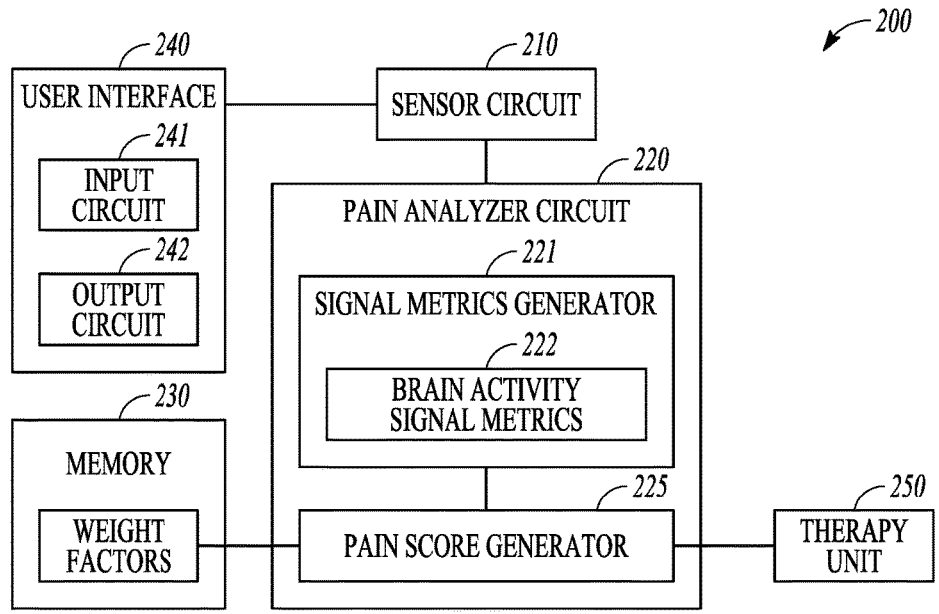
FIG. 2 illustrates, by way of example and not limitation, a block diagram of a pain management system.

FIG. 2 illustrates, by way of example and not limitation, a block diagram of a pain management system 200, which may be an embodiment of the neuromodulation system 100. The pain management system 200 may assess pain of a subject using at least one physiological signal, and program a pain therapy based on the pain assessment. As illustrated in FIG. 2, the pain management system 200 may include a sensor circuit 210, a pain analyzer circuit 220, a memory 230, a user interface 240, and a therapy unit 250.

The sensor circuit 210 may be coupled to one or more physiological sensors to sense from the patient at least one physiological signal. The sensor circuit 210 may include sense amplifier circuit that may pre-process the sensed physiological signals, including, for example, amplification, digitization, filtering, or other signal conditioning operations. Various physiological signals, such as cardiac, pulmonary, neural, or biochemical signals may demonstrate characteristic signal properties in response to an onset, intensity, severity, duration, or patterns of pain. In an example, the sensor circuit 210 may be coupled to implantable or wearable sensors to sense cardiac signals such as electrocardiograph (ECG), intracardiac electrogram, gyrocardiography, magnetocardiography, heart rate signal, heart rate variability signal, cardiovascular pressure signal, or heart sounds signal, among others. In another example, the sensor circuit 210 may sense pulmonary signals such as a respiratory signal, a thoracic impedance signal, or a respiratory sounds signal. In yet another example, the sensor circuit 210 may sense biochemical signals such as blood chemistry measurements or expression levels of one or more biomarkers, which may include, by way of example and not limitation, B-type natriuretic peptide (BNP) or N-terminal pro b-type natriuretic peptide (NT-proBNP), serum cytokine profiles, P2X4 receptor expression levels, gamma-aminobutyric acid (GABA) levels, TNFα and other inflammatory markers, cortisol, adenosine, Glial cell-derived neurotrophic factor (GDNF), Nav 1.3, Nav 1.7, or Tetrahydrobiopterin (BH4) levels, among other biomarkers.

In an example, the sensor circuit 210 may sense at least one signal indicative of patient brain activity. The physiological sensor may be an ambulatory sensor, such as an implantable or wearable sensor associated with the patient, configured to sense brain electromagnetic activity. Alternatively, the physiological sensor may be a bedside monitor of brain electromagnetic activity. The signals sensed by the physiological sensors may include EEG, MEG, or a brain-evoked potential. Examples of sensors for sensing brain electromagnetic activities are discussed below, such as with reference to FIG. 5.

The pain analyzer circuit 220 may generate a pain score using at least the physiological signals received from the sensor circuit 210. The pain analyzer circuit 220 may be implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a general purpose processor that may receive and execute a set of instructions of performing the functions, methods, or techniques described herein.

The pain analyzer circuit 220 may include circuit sets comprising one or more other circuits or sub-circuits that may, alone or in combination, perform the functions, methods or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

As illustrated in FIG. 2, the pain analyzer circuit 220 may include a signal metrics generator 221 and a pain score generator 225. The signal metrics generator 221 may generate one or more brain activity signal metrics 222 from the sensed at least one physiological signal. The signal metrics may include temporal or spatial parameters, statistical parameters, morphological parameters, and spectral parameters extracted from the signal transformed into the frequency domain or other transformed domain. In an example where the sensed physiological signal includes one or more EEG, MEG, or a brain-evoked potential, the signal metrics may be indicative of strength or a pattern of brain electromagnetic activity associated with pain. Examples of the signal metrics for pain quantification are discussed below, such as with reference to FIG. 5.

The pain score generator 225 may generate a pain score using the measurements of the signal metrics generated by the signal metrics generator 221. The pain score can be represented as a numerical or categorical value that quantifies the patient overall pain symptom. In an example, a composite signal metric may be generated using a combination of a plurality of the signal metrics respectively weighted by weight factors. The combination can be linear or nonlinear. The pain score generator 225 may compare the composite signal metric to one or more threshold values or range values, and assign a corresponding pain score (such as numerical values from 0 to 10) based on the comparison.

In another example, the pain score generator 225 may compare the signal metrics to their respective threshold values or range values, assign corresponding signal metric-specific pain scores based on the comparison, and compute a composite pain score using a linear or nonlinear fusion of the signal metric-specific pain scores weighted by their respective weight factors. In an example, the threshold can be inversely proportional to signal metric's sensitivity to pain. A signal metric that is more sensitive to pain may have a corresponding lower threshold and a larger metric-specific pain score, thus plays a more dominant role in the composite pain score than another signal metric that is less sensitive to pain. Examples of the fusion algorithm may include weighted averages, voting, decision trees, or neural networks, among others. The pain score generated by the pain score generator 225 may be output to a system user or a process.

In various examples, in addition to the physiological signals such as the brain electromagnetic activity signals, the sensor circuit 210 may sense one or more functional signals from the patient. Examples of the functional signals may include, but not limited to, patient posture, gait, balance, or physical activity signals, among others. The sensor circuit 210 may sense the functional signals via one or more implantable or wearable motion sensors, including an accelerometer, a gyroscope (which may be a one-, two-, or three-axis gyroscope), a magnetometer (e.g., a compass), an inclinometer, a goniometer, an electromagnetic tracking system (ETS), or a global positioning system (GPS) sensor, among others. Detailed description of functional signals for use in pain characterization are disclosed in commonly assigned U.S. Provisional Patent Application Ser. No. 62/445,075, entitled "PAIN MANAGEMENT BASED ON FUNCTIONAL MEASUREMENTS", the disclosures of which are incorporated herein by reference. The signal metrics generator 221 may generate functional signal metrics from the functional signals, and the pain score generator 225 may determine the pain score using a linear or nonlinear combination of the muscle tension signal metrics and the functional signal metrics. Commonly assigned U.S. Provisional Patent Application Ser. No. 62/445,053, entitled "PAIN MANAGEMENT BASED ON CARDIOVASCULAR PARAMETERS" describes cardiovascular parameters such as arterial pulsatile activity and electrocardiography for use in pain analysis, the disclosure of which is incorporated herein by reference in its entirety. Commonly assigned U.S. Provisional Patent Application Ser. No. 62/445,061, entitled "PAIN MANAGEMENT BASED ON BRAIN ACTIVITY MONITORING" describes information of brain activity for use in pain analysis, the disclosure of which is incorporated herein by reference in its entirety. Commonly assigned U.S. Provisional Patent Application Ser. No. 62/445,069, entitled "PAIN MANAGEMENT BASED ON RESPIRATION-MEDIATED HEART RATES" describes information of respiration-mediated heart rate for use in pain analysis, the disclosure of which is incorporated herein by reference in its entirety. Commonly assigned U.S. Provisional Patent Application Ser. No. 62/445,082, entitled "PAIN MANAGEMENT BASED ON EMOTIONAL EXPRESSION MEASUREMENTS" describes measurements of patient emotional expressions for use in pain analysis, the disclosure of which is incorporated herein by reference in its entirety. Commonly assigned U.S. Provisional Patent Application Ser. No. 62/445,092, entitled "PAIN MANAGEMENT BASED ON MUSCLE TENSION MEASUREMENTS" describes measurements of patient muscle tension including electromyography for use in pain analysis, the disclosure of which is incorporated herein by reference in its entirety. One or more of these additional signals or measurements may be used by the pain analyzer circuit 220 to generate a pain score.

The memory 230 may be configured to store sensor signals or signal metrics such as generated by the sensor circuit 210 and the signal metrics generator 221, and the pain scores such as generated by the pain score generator 225. Data may be stored at the memory 230 continuously, periodically, or triggered by a user command or a specific event. In an example, as illustrated in FIG. 2, the memory 230 may store weight factors, which may be used by the pain score generator 225 to generate the composite pain score. The weight factors may be provided by a system user, or alternatively be automatically determined or adjusted such as based on the corresponding signal metrics' reliability in representing an intensity of the pain. Examples of the automatic weight factor generation are discussed below, such as with reference to FIG. 3.

The user interface 240 may include an input circuit 241 and an output unit 242. In an example, at least a portion of the user interface 240 may be implemented in the external system 130. The input circuit 241 may enable a system user to program the parameters used for sensing the physiological signals, generating signal metrics, or generating the pain score. The input circuit 241 may be coupled to one or more input devices such as a keyboard, on-screen keyboard, mouse, trackball, touchpad, touch-screen, or other pointing or navigating devices. In some example, the input device may be incorporated in a mobile device such as a smart phone or other portable electronic device configured to execute a mobile application ("App"). The mobile App may enable a patient to provide pain description or quantified pain scales during the pain episodes. In an example, the input circuit 241 may enable a user to confirm, reject, or edit the programming of the therapy unit 250, such as parameters for electrostimulation, as to be discussed in the following.

The output unit 242 may include a display to present to a system user such as a clinician the pain score. The output unit 242 may also display information including the physiological signals, trends of the signal metric, or any intermediary results for pain score calculation such as the signal metric-specific pain scores. The information may be presented in a table, a chart, a diagram, or any other types of textual, tabular, or graphical presentation formats, for displaying to a system user. The presentation of the output information may include audio or other human-perceptible media format. In an example, the output unit 242 may generate alerts, alarms, emergency calls, or other forms of warnings to signal the system user about the pain score.

The therapy circuit 250 may be configured to deliver a therapy to the patient based on the pain score generated by the pain score generator 225. The therapy circuit 250 may include an electrostimulator configured to generate electrostimulation energy to treat pain. In an example, the electrostimulator may deliver spinal cord stimulation (SCS) via electrodes electrically coupled to the electrostimulator. The electrodes may be surgically placed at a region at or near a spinal cord tissue, which may include, by way of example and not limitation, dorsal column, dorsal horn, spinal nerve roots such as the dorsal nerve root, dorsal root entry zone, spinothalamic tract, and dorsal root ganglia. The SCS may be in a form of stimulation pulses that are characterized by pulse amplitude, pulse width, stimulation frequency, duration, on-off cycle, pulse shape or waveform, temporal pattern of the stimulation, among other stimulation parameters. Examples of the stimulation pattern may include burst stimulation with substantially identical inter-pulse intervals, or ramp stimulation with incremental inter-pulse intervals or with decremental inter-pulse intervals. In some examples, the frequency or the pulse width may change from pulse to pulse. The electrostimulator may additionally or alternatively deliver electrostimulation to other target tissues such as peripheral nerves tissues. In an example, the electrostimulator may deliver transcutaneous electrical nerve stimulation (TENS) via detachable electrodes that are affixed to the skin.

The therapy circuit 250 may additionally or alternatively include a drug delivery system, such as an intrathecal drug delivery pump that may be surgically placed under the skin, which may be programmed to inject medication or biologics through a catheter to the area around the spinal cord. Other examples of drug delivery system may include a computerized patient-controlled analgesia pump that may deliver the prescribed pain medication to the patient such as via an intravenous line. In some examples, the therapy circuit 250 may be delivered according to the pain score received from the pain score generator 225.

Figure 3:
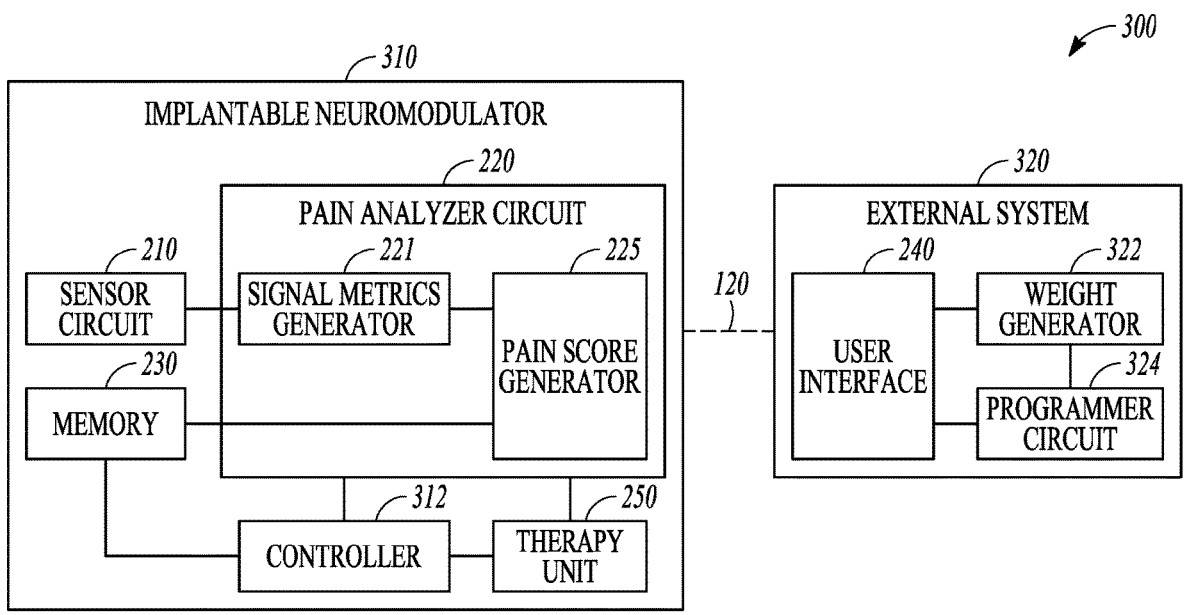
FIG. 3 illustrates, by way of example and not limitation, a block diagram of a pain management system comprising an implantable neuromodulator.

FIG. 3 illustrates, by way of example and not limitation, a block diagram of another example of a pain management system 300, which may be an embodiment of the neuromodulation system 100 or the pain management system 200. The pain management system 300 may include an implantable neuromodulator 310 and an external system 320, which may be, respectively, embodiments of the IND 112 and the external system 130 as illustrated in FIG. 1. Examples of the implantable neuromodulator 310 may include an implantable pulse generator (IPG) for providing SCS therapy, an IPG for providing DBS therapy, or an IPG for providing peripheral nerve stimulation (PNS) therapy. The external system 320 may be communicatively coupled to the implantable neuromodulator 310 via the communication link 120.

The implantable neuromodulator 310 may include several components of the pain management system 200 as illustrated in FIG. 2, including the sensor circuit 210, the pain analyzer circuit 220, the memory 230, and the therapy unit 250. The sensor circuit 210 may be communicatively coupled, via a wired or wireless connection, to one or more implantable or wearable sensors configured to sense brain electromagnetic activities such as EEG signals. The EEG signals may be recorded from multiple electrodes placed on the scalp. In some examples, the EEG signals may include intracranial EEG, also known as electrocorticography (ECoG), by using an array of electrodes positioned directly on the cortical surface of the brain to record electrical activity from the cerebral cortex. Examples of the sensors for sensing EEG signals are discussed below with reference to FIG. 5. As discussed with reference to FIG. 2, the pain analyzer circuit 220 includes the pain score generator 225 that determines a pain score using weight factors stored in the memory 230 and the signal metrics from the signal metrics generator 221 which may also be included in the pain analyzer circuit 220. The implantable neuromodulator 310 may include a controller circuit 312, coupled to the therapy unit 250, that controls the generation and delivery of pain therapy, such as neurostimulation energy. The controller circuit 312 may control the generation of electrostimulation pulses according to specific stimulation parameters. The stimulation parameters may be provided by a system user. Alternatively, the stimulation parameters may be automatically determined based on the intensity, severity, duration, or pattern of pain, which may be subjectively described by the patient or automatically quantified based on the physiological signals sensed by the sensor circuit 210. For example, when a patient-described or sensor-indicated quantification exceeds a respective threshold value or falls within a specific range indicating elevated pain, the electrostimulation energy may be increased to provide stronger pain relief. Increased electrostimulation energy may be achieved by programming a higher pulse intensity, a higher frequency, or a longer stimulation duration or "on" cycle, among others. Conversely, when a patient-described or sensor-indicated pain quantification falls below a respective threshold value or falls within a specific range indicating no pain or mild pain, the electrostimulation energy may be decreased. The controller circuit 312 may also adjust stimulation parameters to alleviate side effects introduced by the electrostimulation of the target tissue.

Additionally or alternatively, the controller circuit 312 may control the therapy unit 250 to deliver electrostimulation pulses via specific electrodes. In an example of pain management via SCS, a plurality of segmented electrodes, such as the electrodes 116, may be distributed in one or more leads. The controller circuit 312 may configure the therapy unit 250 to deliver electrostimulation pulses via a set of electrodes selected from the plurality of electrodes. The electrodes may be manually selected by a system user or automatically selected based on the pain score. Examples of selecting electrodes for electrostimulation based on the pain score are discussed below, such as with reference to FIGS. 4A-B.

The implantable neuromodulator 310 may receive the information about electrostimulation parameters and the electrode configuration from the external system 320 via the communication link 120. Additional parameters associated with operation of the therapy unit 250, such as battery status, lead impedance and integrity, or device diagnostic of the implantable neuromodulator 310, may be transmitted to the external system 320. The controller circuit 312 may control the generation and delivery of electrostimulation using the information about electrostimulation parameters and the electrode configuration from the external system 320. Examples of the electrostimulation parameters and electrode configuration may include: temporal modulation parameters such as pulse amplitude, pulse width, pulse rate, or burst intensity; morphological modulation parameters respectively defining one or more portions of stimulation waveform morphology such as amplitude of different phases or pulses included in a stimulation burst; or spatial modulation parameters such as selection of active electrodes, electrode combinations which define the electrodes that are activated as anodes (positive), cathodes (negative), and turned off (zero), and stimulation energy fractionalization which defines amount of current, voltage, or energy assigned to each active electrode and thereby determines spatial distribution of the modulation field.

In an example, the controller circuit 312 may control the generation and delivery of electrostimulation in a closed-loop fashion by adaptively adjusting one or more stimulation parameters or stimulation electrode configuration based on the pain score. For example, if the score exceeds the pain threshold (or falls within a specific range indicating an elevated pain), then the first electrostimulation may be delivered. Conversely, if the composite pain score falls below a respective threshold value (or falls within a specific range indicating no pain or mild pain), then a second pain therapy, such as second electrostimulation may be delivered. The first and second electrostimulations may differ in at least one of the stimulation energy, pulse amplitude, pulse width, stimulation frequency, duration, on-off cycle, pulse shape or waveform, electrostimulation pattern such as electrode configuration or energy fractionalization among active electrodes, among other stimulation parameters. In an example, the first electrostimulation may have higher energy than the second electrostimulation, such as to provide stronger effect of pain relief. Examples of increased electrostimulation energy may include a higher pulse intensity, a higher frequency, and a longer stimulation duration or "on" cycle, among others.

The parameter adjustment or stimulation electrode configuration may be executed continuously, periodically at specific time, duration, or frequency, or in a commanded mode upon receiving from a system user a command or confirmation of parameter adjustment. In some examples, the closed-loop control of the electrostimulation may be further based on the type of the pain, such as chronic or acute pain. In an example, the pain analyzer circuit 220 may trend the signal metric over time to compute an indication of abruptness of change of the signal metrics, such as a rate of change over a specific time period. The pain episode may be characterized as acute pain if the signal metric changes abruptly (e.g., the rate of change of the signal metric exceeding a threshold), or as chronic pain if the signal metric changes gradually (e.g., the rate of change of the signal metric falling below a threshold). The controller circuit 312 may control the therapy unit 250 to deliver, withhold, or otherwise modify the pain therapy in accordance with the pain type. For example, incidents such as toe stubbing or bodily injuries may cause abrupt changes in certain signal metrics, but no adjustment of the closed-loop pain therapy is deemed necessary. On the contrary, if the pain analyzer circuit 220 detects chronic pain characterized by gradual signal metric change, then the closed-loop pain therapy may be delivered accordingly.

The adaptive adjustment of stimulation parameters or stimulation electrode based on the pain score as discussed above may be based on paresthesia effect, that is, patient perception of stimulation and its effect on pain. The adaptive adjustment may provide desired paresthesia coverage while minimizing patient comfort and/or energy usage. In some examples, the controller circuit 312 may adjust stimulation parameters or stimulation electrode for sub-perception stimulation (e.g., sub-perception SCS) using the sensed brain activity. In contrast to supra-perception stimulation where paresthesia may be readily felt by the patient, sub-perception stimulation may take several hours or over a day before a patient may be able to assess the therapeutic effect of the stimulation. Electrode location or other stimulation parameters may be varied, while the pain analyzer circuit 220 may monitor the brain activity for indicators that predict stimulation efficacy, such as based on a comparison to the brain activity signal template representative of effective prevention of pain sensation. Even though the pain might not be reduced yet by stimulation, the brain activity may show early indications that predict the therapeutic effect of pain relief.

The external system 320 may include the user interface 240, a weight generator 322, and a programmer circuit 324. The weight generator 322 may generate weight factors used by the pain score generator 225 to generate the pain score. The weight factors may indicate the signal metrics' reliability in representing an intensity of the pain. A sensor metric that is more reliable, or more sensitive or specific to the pain, would be assigned a larger weight than another sensor metric that is less reliable, or less sensitive or specific to the pain. In an example, the weight factors may be proportional to correlations between a plurality of quantified pain scales (such as reported by a patient) and measurements of the measurements of the signal metrics corresponding to the plurality of quantified pain scales. A signal metric that correlates with the pain scales is deemed a more reliable signal metric for pain quantification, and is assigned a larger weight factor than another signal metric less correlated with the quantified pain scales. In another example, the weight generator 322 may determine weight factors using the signal sensitivity to pain. The signal metrics may be trended over time, such as over approximately six months. The signal sensitivity to pain may be represented by a rate of change of the signal metrics over time during a pain episode. The signal sensitivity to pain may be evaluated under a controlled condition such as when the patient posture or activity is at a specific level or during specific time of the day. The weight generator 322 may determine weight factors to be proportional to signal metric's sensitivity to pain.

The programmer circuit 324 may produce parameter values for operating the implantable neuromodulator 310, including parameters for sensing physiological signals and generating signal metrics, and parameters or electrode configurations for electrostimulation. In an example, the programmer circuit 324 may generate the stimulation parameters or electrode configurations for SCS based on the pain score produced by the pain score generator 225. Through the communication link 120, the programmer circuit 324 may continuously or periodically provide adjusted stimulation parameters or electrode configuration to the implantable neuromodulator 210. By way of non-limiting example and as illustrated in FIG. 3, the programmer circuit 324 may be coupled to the user interface 234 to allow a user to confirm, reject, or edit the stimulation parameters, sensing parameters, or other parameters controlling the operation of the implantable neuromodulator 210. The programmer circuit 324 may also adjust the stimulation parameter or electrode configuration in a commanded mode upon receiving from a system user a command or confirmation of parameter adjustment.

The programmer circuit 324, which may be coupled to the weight generator 322, may initiate a transmission of the weight factors generated by the weight generator 322 to the implantable neuromodulator 310, and store the weight factors in the memory 230. In an example, the weight factors received from the external system 320 may be compared to previously stored weight factors in the memory 230. The controller circuit 312 may update the weight factors stored in the memory 230 if the received weight factors are different than the stored weights. The pain analyzer circuit 220 may use the updated weight factors to generate a pain score. In an example, the update of the stored weight factors may be performed continuously, periodically, or in a commanded mode upon receiving a command from a user. In various examples, weight factors may be updated using a fusion model. Commonly assigned U.S. Provisional Patent Application Ser. No. 62/445,095, entitled "PATIENT-SPECIFIC CALIBRATION OF PAIN QUANTIFICATION" describes systems and methods for calibrating a fusion model, such as adjusting weights for signal metrics, using a reference pain quantification, the disclosure of which is incorporated herein by reference in its entirety.

In some examples, the pain score may be used by a therapy unit (such as an electrostimulator) separated from the pain management system 300. In various examples, the pain management system 300 may be configured as a monitoring system for pain characterization and quantification without delivering closed-loop electrostimulation or other modalities of pain therapy. The pain characterization and quantification may be provided to a system user such as the patient or a clinician, or to a process including, for example, an instance of a computer program executable in a microprocessor. In an example, the process includes computer-implemented generation of recommendations or an alert to the system user regarding pain medication (e.g., medication dosage and time for taking a dose), electrostimulation therapy, or other pain management regimens. The therapy recommendations or alert may be based on the pain score, and may be presented to the patient or the clinician in various settings including in-office assessments (e.g. spinal cord stimulation programming optimization), in-hospital monitoring (e.g. opioid dosing during surgery), or ambulatory monitoring (e.g. pharmaceutical dosing recommendations).

In an example, in response to the pain score exceeding a threshold which indicates elevated pain symptom, an alert may be generated and presented at the user interface 240 to remind the patient to take pain medication. In another example, therapy recommendations or alerts may be based on information about wearing-off effect of pain medication, which may be stored in the memory 230 or received from the user interface 240. When the drug effect has worn off, an alert may be generated to remind the patient to take another dose or to request a clinician review of the pain prescription. In yet another example, before a pain therapy such as neurostimulation therapy is adjusted (such as based on the pain score) and delivered to the patient, an alert may be generated to forewarn the patient or the clinician of any impending adverse events. This may be useful as some pain medication may have fatal or debilitating side effects. In some examples, the pain management system 300 may identify effect of pain medication addiction such as based on patient physiological or functional signals. An alert may be generated to warn the patient about effects of medication addiction and thus allow medical intervention.

In some examples, the pain analyzer circuit 220 may be alternatively included in the external system 320. The pain analyzer circuit 220, or a portion of the pain analyzer circuit 220 such as the signal metrics generator 221 or the pain score generator 225, may be included in a wearable device configured to be worn or carried by a subject. At least a portion of the sensor circuit 210 may also be included in the external system 320, such that the physiological signal indicative of brain electromagnetic activities that are sensed by one or more physiological sensors (e.g., ambulatory EEG sensors or bedside EEG sensors) may be transmitted to the external system 320 for processing, and generating the pain score based on the processed brain electromagnetic activity signals. A clinician may use the external system 320 to program the implantable neuromodulator 310 with appropriate pain therapy based on the pain score generated at the external system 320, such as during a clinical trial or patient follow-up visit at the clinic.

Figure 4A:
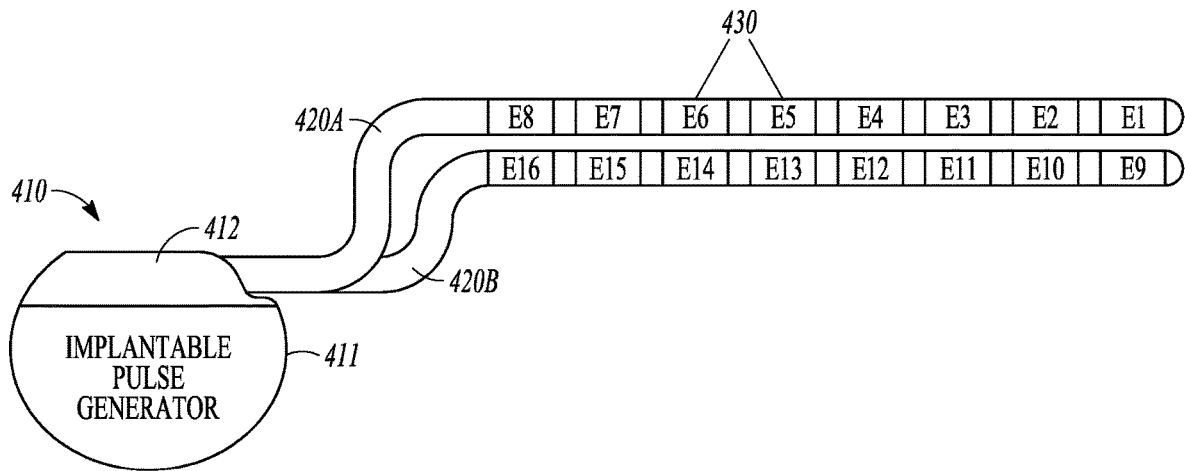
FIGS. 4A-B illustrate, by way of example and not limitation, block diagrams of selecting active electrodes for delivering pain-relief electrostimulation energy based on the pain score.
Figure 4B:
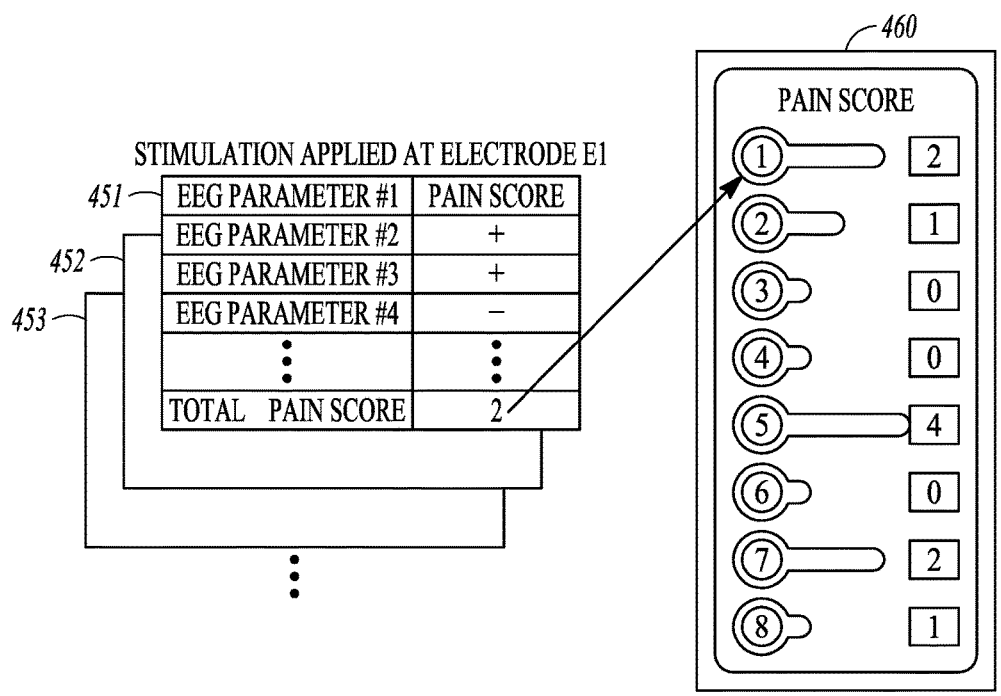

FIGS. 4A-B illustrate, by way of example and not limitation, block diagrams of portions of a system for selecting active electrodes for delivering pain-relief electrostimulation energy based on the pain score. FIG. 4A illustrates an IPG 410 operably coupled to two neuromodulation leads 420A-B via a header 412. The IPG 410 can be an embodiment of the IPG 110 as shown in FIG. 1. The IPG 410 includes a can housing 411 that encloses circuitry and other components for sensing physiological signals, delivering electrostimulations, and controlling other device operations. The neuromodulation leads 420A-B each includes a plurality of electrodes 430 axially disposed an elongated cylindrical lead body. The electrodes 430 may be used for delivering neuromodulation of a specific target tissue, such as SCS at a spinal cord region, DBS at a brain region, or PNS at or next to a peripheral nerve. The electrodes 430 may take the form of column electrodes (or ring electrodes) or circumferentially segmented electrodes with specified electrode size, shape, and inter-electrode spacing along the length of the respective lead body. By way of example and not limitation, the lead 420A may carry electrodes E1-E8, and the lead 420B may carry electrodes E9-E16. In some examples, at least some of the electrodes 430 may also be coupled to a sensor circuit to sense tissue electrical activity, such as brain activity or neural activity at or near the spinal cord.

FIG. 4B illustrates a diagram of electrode selection for delivering pain-relief electrostimulation from a plurality of candidate electrodes such as the electrodes 430 on one or both of the neuromodulation leads 420A-B. The electrode selection may be performed using the pain management system 200 or 300. The electrode selection may be based on relative pain-reduction effects when electrostimulation energy is delivered according to configurations involving one or more of the candidate electrodes.

The pain episode may include spontaneous pain experienced in patient daily life. Alternatively, a pain episode may be induced such as in a clinic and administered by a clinician. In an example, pain may be induced by delivering electrostimulation energy according to a pre-determined stimulation protocol. The pre-determined stimulation protocol may include a plurality of electrode configurations arranged in a specified order. Each electrode configuration may include a designation of an anode and a cathode, each selected from the candidate electrodes (such as some or all of the electrodes 430) and a reference electrode such as the device can housing 411. In an example, the electrode configuration includes a unipolar configuration with one of the candidate electrodes (such as E1-E16) designated as a cathode and the device can housing 411 as an anode. In another example, the electrode configuration includes a bipolar configuration with one of the candidate electrodes (such as E1-E16) designated as a cathode and another candidate electrode, different than the cathode, as an anode. In some examples, pain may be induced by temporarily withholding pain-relief therapy (such as electrostimulation) or varying therapy dosage to achieve intermediate levels of pain reduction effect. Additionally or alternatively, pain induction procedure may include applying heat, pressure, or other artificial stimuli during quantitative sensory testing, administering nerve block or adjusting pharmaceutical agents, psychological or stress stimulation, or physical exercise such as strenuous leg lift or grip test, among others.

A pain assessment session may be initiated to analyze patient perception and physiological responses to the spontaneous or induced pain episodes. The pain assessment session may be automatically triggered by a sensor indicator, or activated manually by the patient (such as during a spontaneous pain episode) or a clinician (such as during an induced pain episode). The pain assessment session may include evaluating the electrostimulation's pain-relief effect.

During the pain assessment session, physiological signals indicative of patient brain activity, such as an EEG signal, may be recorded during the pain-relief electrostimulation according to each of the electrode configurations in the pre-determined stimulation protocol, and analyzed such as using the pain management system 200 or 300, 1. A plurality of EEG parameters may be extracted from the sensed EEG signal, such as using the signal metrics generator 221. By way of example and not limitation, a pain score report 451 includes metric-specific pain scores corresponding to pain-relief electrostimulation applied according to an electrode configuration with electrode E1 as a cathode and the can housing 411 as an anode. The metric-specific pain scores may be determined by comparing the respective signal metrics, i.e., the EEG parameters, to their respective threshold values. A positive indicator "+", or a metric-specific numerical score of "1", is assigned for an EEG parameter if that EEG parameter exceeds its respective threshold value, indicating pain persistence or undesirable pain reduction. Conversely, a negative indicator "−", or a metric-specific numerical score of "0", is assigned for an EEG parameter if that EEG parameter falls below its respective threshold value and indicates no pain or desirable pain reduction. A composite pain score may be computed using a combination of the metric-specific pain scores corresponding to the EEG parameters evaluated. In an example, the composite pain score may be computed as a sum or weighted sum of the metric-specific pain scores. In the illustrated example in FIG. 4B, a total score of "2" is obtained for the electrode configuration involving electrode E1.

The above illustrated process may similarly be performed for other electrode configurations, which may result in a pain score report 452 with a composite pain score of "1" for electrode configuration involving electrode E2, another pain score report 453 with a composite pain score of "0" for electrode configuration involving electrode E3, and so on. The composite pain scores associated with the electrode configurations included in the stimulation protocol may be presented to the patient or a clinician, such as in a form of a table 460. In lieu of or in addition to the numerical pain scores, graphical representations, such as a colored bar representing the composite pain scores, may be included in the table 460. In the example illustrated in FIG. 4B, the electrode E5 corresponds to a pain score of "4", which is the highest among the tested electrodes E1-E8, indicating the least effectiveness in pain reduction compared to pain-relief electrostimulation delivered according to electrode configurations involving other electrodes different from electrode E5. The electrodes E3, E4 and E6 each corresponds to a pain score of "0", the lowest among the tested electrodes E1-E8, indicating the highest effectiveness in pain reduction. As such, in a closed-loop pain therapy or clinician programmed pain therapy, the electrode E5 may be excluded, and at least one of the electrodes E3, E4 or E6 may be selected as active electrodes (such as cathodes) for delivering electrostimulation energy.

In some examples, as an alternative of the metric-specific pain score, a metric-specific pain reduction score may be determined for each EEG parameter. A pain reduction score of "1" is assigned if the EEG parameter indicates pain relief (or desirable pain reduction) and a pain reduction score of "0" is assigned if the EEG parameter indicates pain persistence (or undesirable pain reduction). A composite pain reduction score may be computed using a combination of the metric-specific pain reduction scores. One or more electrodes that correspond to the highest composite pain reduction score among the tested electrodes E1-E8 indicate the highest effectiveness in pain reduction, and may be selected as active electrodes (such as cathodes) for delivering electrostimulation energy.

The above-discussed electrode selection based on pain scores associated with EEG parameters may be modified for selecting, or determining values of, one or more other therapy parameters, including: electrode energy fractionalization which defines amount of current, voltage, or energy assigned to each active electrode and thereby determines spatial distribution of the modulation field; temporal modulation parameters such as pulse amplitude, pulse width, pulse rate, or burst intensity; morphological modulation parameters respectively defining one or more portions of stimulation waveform morphology such as amplitude of different phases or pulses included in a stimulation burst, among others. The disclosed method may also be used in selecting one or more active therapy regimes from a plurality of candidate therapy regimes each involving a combination of multiple therapy parameters such as electrode selection, energy fractionalization, waveform temporal and morphological parameters. For example, in an automated closed-loop pain therapy or clinician programmed pain therapy, a particular value for a specific therapy parameter, or a particular therapy regime, may be selected and programmed to the IPG 411 for delivering electrostimulation therapy to relieve patient pain.

Figure 5:
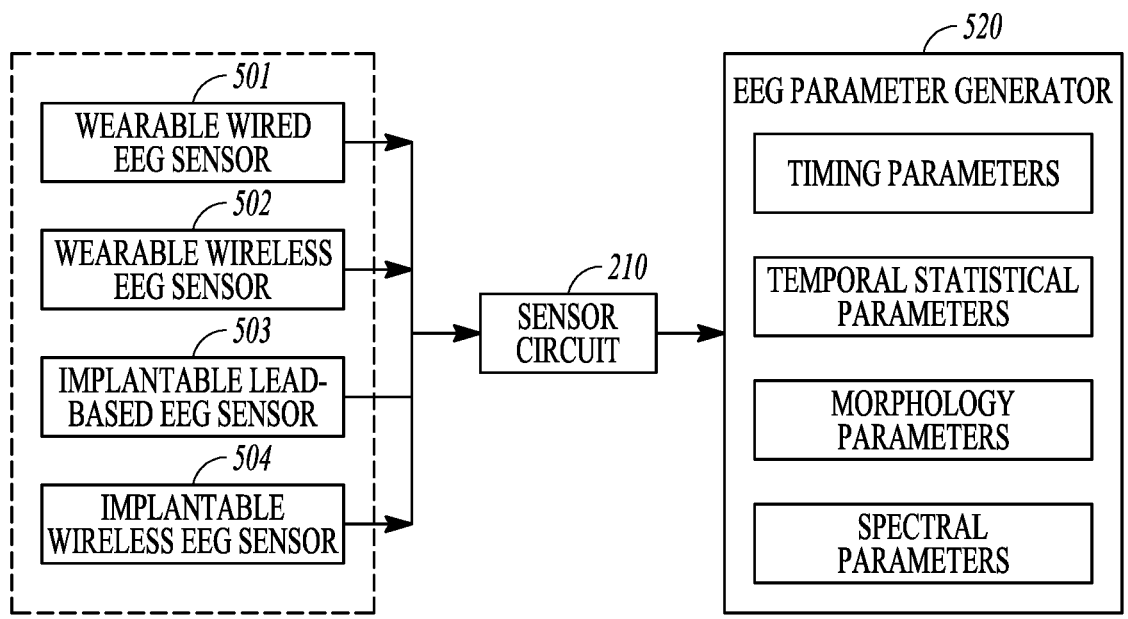
FIG. 5 illustrates, by way of example and not limitation, a block diagram of a portion of the system for sensing brain electromagnetic activities such as an EEG and generating EEG parameters for pain quantification.

FIG. 5 illustrates, by way of example and not limitation, a block diagram of a portion of the system for sensing brain electromagnetic activities such as an EEG and generating EEG parameters for pain quantification. The EEG parameters may be used by the pain management system 200 or 300 to characterize and quantify patient pain. The system portion may include one or more EEG sensors 501 through 504, the sensor circuit 210, and an EEG parameter generator 520 which is an embodiment of the signal metrics generator 221.

One or more types of EEG sensors may be used to sense the EEG signals. According to the manner of interaction with the patient, the EEG sensors may include, by way of example and not limitation, one or more of a wearable wired EEG sensor 501, a wearable wireless EEG sensor 502, an implantable lead-based EEG sensor 503, or an implantable wireless EEG sensors 504.

The wearable wired EEG sensor 501 may be worn on a patient head and connected to a bedside stationary EEG monitor. An example of the wearable wired EEG sensor 501 may include an EEG cap with scalp electrodes mounted thereon such as according to the international 10-20 system. The wearable wireless EEG sensor 502 may be mounted on a removable headwear, such as a cap, a hat, a headband, or eye glasses, among others. Alternatively, the wearable wireless EEG sensor 502 may be mounted on a removable accessory such as an earpiece, an ear plug, or an ear patch. The earpiece may be personalized to allow tight fit within patient concha and ear cannel and secure electrode-tissue contact. Alternatively, the electrodes may be placed close to the ear such as hidden behind the ear lobe. The implantable lead-based EEG sensors 503 may include electrodes disposed on an implantable lead configured to be positioned on a target tissue site for therapeutic electrostimulation, such as a lead configured to be implanted in patient brain for DBS, or a lead implanted at a head location to provide occipital or trigeminal PNS. The electrodes may not only be used to provide electrostimulation energy at the implanted sites to treat pain, but can also be coupled to a sensor circuit to sense brain activity such as an EEG. An example of the implantable-lead based EEG sensors is illustrated in FIG. 4A. The implantable wireless EEG sensor 504 may be subcutaneously implanted at a head location to sense an EEG signal. The wearable wireless EEG sensor 502 and the implantable wireless EEG sensor 504 may each include a transmitter circuit configured for transmitting the sensed EEG signal to the sensor circuit 210 or the IPG 411 via a wireless communication link, such as a Bluetooth protocol, an inductive telemetry link, a radio-frequency telemetry link, Ethernet, or IEEE 802.11 wireless, among others.

The sensor circuit 210 may be communicatively coupled to the one or more EEG sensors 501-504 via a wired or wireless connection. The sensor circuit 210 may include sense amplifier circuit that may pre-process the sensed EEG signal. From the processed physiological signals, the EEG parameter generator 520 may extract one or more EEG parameters. In an example, at least a part of the sensor circuit 210 or the EEG parameter generator 520 may be implemented in, and executed by, a mobile device. Examples of the mobile device may include a smart phone, a wearable device, a fitness band, a portable health monitor, a tablet, a laptop computer, or other types of portable computerized device. Alternatively, at least a part of the sensor circuit 210 or the EEG parameter generator 520 may be included in a wearable device incorporating signal processing circuitry to analyzing the EEG signals and generating pain scores. The wearable device may be worn or otherwise associated on the wrist, arm, upper or lower leg, trunk, or other body part suitable for a tight or loose belt-band containing the wearable, or located inside a wallet, a purse, or other handheld accessories.

The EEG parameter generator 520 may generate one or more EEG parameters from the sensed EEG signal. By way of example and not limitation, the EEG parameters may include timing parameters, temporal statistical parameters, morphology parameters, and spectral parameters. Examples of the timing parameters may include a time interval between a first characteristic point in one signal and a second characteristic point in another signal. Examples of the statistical parameters may include signal mean, median, or other central tendency measures or a histogram of the signal intensity, variance, standard deviation, or higher-order statistics, among others. Examples of the morphological parameters may include maximum or minimum within a specific time period such as a cardiac cycle, positive or negative slope, among others.

In some examples, the sensor circuit 210 may perform signal transformation on the sensed EEG signal, such as a Fourier transform or wavelet transform. One or more signal metrics may be extracted from the transformed EEG signals, which may include signal power spectra at specific frequency bands, dominant frequency, coherence, spectral entropy, mutual information, frequency shift of spectral peaks, spectral width or a Q-factor of power spectra, or other features extracted from the frequency domain or other transformed domain. In an example, multiple epochs of EEG recordings, each having a specified duration, may be collected. The sensor circuit 210 may include a filter bank comprising filters with respective characteristics such as passbands and center frequencies. In an example, each epoch of EEG recording may be filtered through the filter bank to obtain one or more of: a delta wave within a frequency band of approximately 1-4 Hertz (Hz), a theta wave within a frequency band of approximately 4-7 Hz, an alpha wave within a frequency band of approximately 8-15 Hz, or a beta wave within a frequency band of approximately 16-30 Hz, among others. The EEG parameters may include power spectra, dominant frequency, or other spectral parameters of these distinct EEG waves at distinct frequency bands averaged over the multiple epochs. In some examples, EEG signals may be collected from various brain regions of interest, which may include frontal, central, parietal, occipital, and temporal regions. The EEG parameters may include power spectra, dominant frequency, or other spectral parameters of the distinct EEG waves corresponding to different brain regions of interest. The pain score generator 225 may generate pain score at least based on the EEG parameters.

Figure 6:
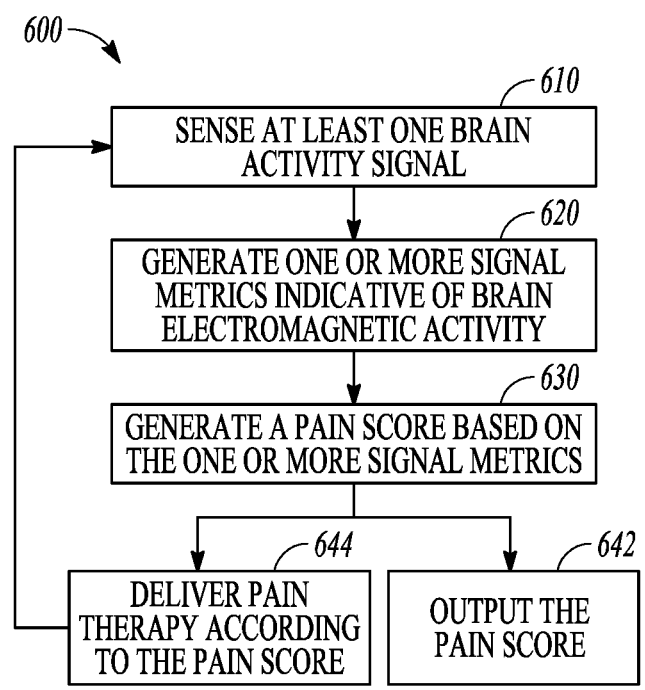
FIG. 6 illustrates, by way of example and not limitation, a flow chart of a method for managing pain in a patient.

FIG. 6 illustrates, by way of example and not limitation, a method 600 for managing pain of a patient. The method 600 may be implemented in a medical system, such as the pain management system 200 or 300. In an example, at least a portion of the method 600 may be executed by a neuromodulator device (IND) such as the implantable neuromodulator 310. In an example, at least a portion of the method 600 may be executed by an external programmer or remote server-based patient management system, such as the external system 320 that are communicatively coupled to the IND. The method 600 may be used to provide neuromodulation therapy to treat chronic pain or other disorders.

The method 600 begins at step 610, where at least one physiological signal indicative of patient brain activity may be sensed from the patient, such as using the sensor circuit 210. Examples of the brain activity signal may include electroencephalography (EEG), magnetoencephalography (MEG), or a brain-evoked potential, among other brain electromagnetic signals. The brain activity signals may be associated with patient pain vulnerability to experience chronic pain. Therefore, monitoring of patient brain electromagnetic activity may provide an objective assessment of pain. The brain activity signal may be sensed via an implantable or wearable sensor associated with the patient, such as one or more of the EEG sensors 501-504 as illustrated in FIG. 5 for sensing EEG signals using implantable electrodes or sensors, or non-invasive surface electrodes or sensors. In some examples, the EEG signals may be collected from various brain regions of interest, which may include frontal, central, parietal, occipital, and temporal regions. The brain activity signal may alternatively be sensed via a bedside monitor such as an EEG monitor. In various examples, other physiological signals may additionally be sensed at 610, including, for example, cardiac, pulmonary, neural, or biochemical signals each having characteristic signal properties indicative of onset, intensity, severity, duration, or patterns of pain. In some examples, in addition to the brain activity signals and other physiological signals, one or more functional signals may be sensed at 610, such as via one or more implantable or wearable motion sensors. Examples of the functional signals may include patient posture, gait, balance, or physical activity signals, among others. The functional signals may be used together with the brain activity signal in assessing patient pain.

At 620, one or more signal metrics may be generated from the sensed one or more brain activity signals. The signal metrics may include temporal or spatial parameters, statistical parameters, or morphological parameters. In an example where the sensed physiological signal includes one or more EEG, MEG, or a brain-evoked potential, the signal metrics may be indicative of strength or a pattern of brain electromagnetic activity associated with pain. In some example, the sensed at least one brain activity signal may be processed by applying a signal transformation such as Fourier transform or wavelet transform. One or more signal metrics may be extracted from the transformed signals, such as signal power spectra at specific frequency bands, dominant frequency, coherence, spectral entropy, mutual information, frequency shift of spectral peaks, spectral width or a Q-factor of power spectra, or other features.

In an example, the signal metrics may include one or more of EEG timing parameters, EEG temporal statistical parameters, EEG morphology parameters, or EEG power spectral parameters, as illustrated in FIG. 5. The EEG power spectra at a plurality of frequency bands correspond to distinct EEG components, including a delta wave at approximately 1-4 Hz, a theta wave at approximately 4-7 Hz, an alpha wave at approximately 8-15 Hz, or a beta wave at approximately 16-30 Hz, among others. In some examples, the EEG parameters may include respective spectral parameters corresponding to different brain regions of interest.

At 630, a pain score may be generated using the measurements of the signal metrics indicative of brain electromagnetic activity. The pain score may be represented as a numerical or categorical value that quantifies overall pain quality in the subject. In an example, a composite signal metric may be generated using a combination of the signal metrics weighted by their respective weight factors. The composite signal metric may be categorized as one of a number of degrees of pain by comparing the composite signal metric to one or more threshold values or range values, and a corresponding pain score may be assigned based on the comparison. In another example, the signal metrics may be compared to their respective threshold values or range values and a corresponding signal metric-specific pain score may be determined. A composite pain score may be generated using a linear or nonlinear fusion of the signal metric-specific pain scores each weighted by their respective weight factors. In some examples, the pain score may be computed using a subset of the signal metrics selected based on their temporal profile of pain response. Signal metrics with quick pain response (or a shorter transient state of response) may be selected to compute the pain score during a pain episode. Signal metrics with slow or delayed pain response (or a longer transient state of response before reaching a steady state) may be used to compute the pain score after an extended period following the onset of pain such as to allow the signal metrics to reach steady state of response. In some examples, patient demographic information such as patient age or gender may be used in computing the pain score. A higher pain threshold for the composite signal metric may be selected for male patients than for female patients. Additionally or alternatively, the respective weight factors may be determined based on patient demographic information. The weight factors for the signal metrics may be tuned to a lower value than the weight factors for the same signal metric in a female patient.

At 642, the pain score may be output to a user or to a process, such as via the output unit 242 as illustrated in FIG. 2. The pain score, including the composite pain score and optionally together with metric-specific pain scores, may be displayed on a display screen. Other information such as the brain activity signals and the signal metrics extracted from the brain activity signals may also be output for display or for further processing. In some examples, alerts, alarms, emergency calls, or other forms of warnings may be generated to signal the system user about occurrence of a pain episode or aggravation of pain as indicated by the pain score.

The method 600 may include, at 644, an additional step of delivering a pain therapy to the patient according to the pain score. The pain therapy may include electrostimulation therapy, such as spinal cord stimulation (SC S) via electrodes electrically coupled to the electrostimulator. The SCS may be in a form of stimulation pulses that are characterized by pulse amplitude, pulse width, stimulation frequency, duration, on-off cycle, waveform, among other stimulation parameters. Other electrostimulation therapy, such as one or a combination of DBS, FES, VNS, TNS, or PNS at various locations, may be delivered for pain management. The pain therapy may additionally or alternatively include a drug therapy such as delivered by using an intrathecal drug delivery pump.

In various examples, the pain therapy (such as in the form of electrostimulation or drug therapy) may be delivered in a closed-loop fashion. Therapy parameters, such as stimulation waveform parameters, stimulation electrode combination and fractionalization, drug dosage, may be adaptively adjusted based at least on the pain score. The pain-relief effect of the delivered pain therapy may be assessed based on the signal metrics such as the cardiovascular parameters, and the therapy may be adjusted to achieve desirable pain relief. The therapy adjustment may be executed continuously, periodically at specific time, duration, or frequency, or in a commanded mode upon receiving from a system user a command or confirmation of parameter adjustment. In an example, if the pain score exceeds the pain threshold (or falls within a specific range indicating an elevated pain), then the first electrostimulation may be delivered. Conversely, if the composite pain score falls below a respective threshold value (or falls within a specific range indicating no pain or mild pain), then a second pain therapy, such as second electrostimulation may be delivered. The first and second electrostimulations may differ in at least one of the stimulation energy, pulse amplitude, pulse width, stimulation frequency, duration, on-off cycle, pulse shape or waveform, electrostimulation pattern such as electrode configuration or energy fractionalization among active electrodes, among other stimulation parameters. In some examples, the therapy adjustment may include selecting a set of electrodes, based on the pain scores, from a plurality of candidate electrodes disposed along the length of an implantable lead. The electrodes may be manually selected by a system user, or automatically selected based on a comparison of the pain scores associated with pain-relief electrostimulation delivered via the respective candidate electrodes. Examples of electrode selection method based on the pain scores are discussed below, such as with reference to FIG. 7.

The method 600 may proceed at 610 to sense functional signals in response to the therapy delivered at 644. In some examples, the responses of the signal metrics to pain therapy delivered at 644 may be used to gauge composite pain score computation such as by adjusting the weight factors. In an example, weight factors may be determined and adjusted via the weight generator 322 as illustrated in FIG. 3, to be proportional to signal metric's sensitivity to pain.

Figure 7:
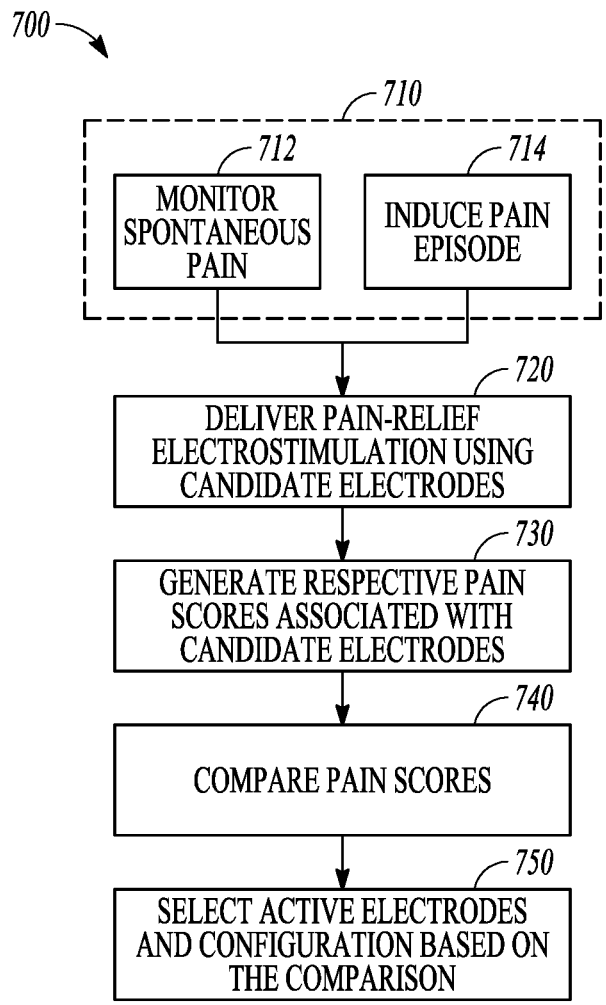
FIG. 7 illustrates, by way of example of not limitation, a flow chart of a method for selecting one or more active electrodes for delivering electrostimulation for pain therapy.

FIG. 7 illustrates, by way of example and not limitation, a method 700 for selecting one or more active electrodes for delivering electrostimulation for pain therapy. The electrode selection may be based on pain scores generated based on physiological signals sensed during a pain episode. The method 700 may be implemented in a medical system, such as the pain management system 200 or 300. In an example, at least a portion of the method 700 may be executed by a neuromodulator device (IND) such as the implantable neuromodulator 310. In an example, at least a portion of the method 700 may be executed by the external system 320 that are communicatively coupled to the IND. The external system 320 may include an external programmer, a wearable device, or a remote server-based patient management system, among others.

The method 700 begins at 710, where one or more pain episodes may be monitored or induced. Spontaneous pain episodes that occur in an ambulatory setting in patient daily life may be monitored at 712 such as using one or more physiological sensors. Additionally or alternatively, one or more pain episodes may be induced at 712. Pain induction may be performed in a clinic and administered by a medical professional. Examples of the pain induction procedure may include applying heat, pressure, or other artificial stimuli during quantitative sensory testing, administering nerve block or adjusting pharmaceutical agents, temporarily withholding pain-relief therapy or varying therapy dosage to achieve intermediate levels of pain reduction effect, psychological or stress stimulation, or physical exercise such as strenuous leg lift or grip test, among others.

At 720, a pain assessment session may be initiated during spontaneous or induced pain, either automatically triggered by a sensor indicator or activated manually by the patient (such as during a spontaneous pain episode) or a clinician (such as during a induced pain episode). The pain assessment session may include delivering electrostimulation energy according to a pre-determined stimulation protocol, and evaluating the electrostimulation's pain-relief effect. The pre-determined stimulation protocol may include a plurality of electrode configurations arranged in a specified order. Each electrode configuration includes an anode and a cathode, each selected from a plurality of candidate electrodes (such as electrodes E1-E16 in FIG. 4A) and a reference electrode (such as the device can housing 411 in FIG. 4A).

At 730, at least one physiological signal indicative of patient brain activity may be sensed during the pain assessment session, such as using the pain management system 200 or 300. In an example, an EEG signal may be recorded during the pain-relief electrostimulation according to each of the electrode configurations in the pre-determined stimulation protocol. EEG parameters may be extracted from the sensed EEG signal such as using the signal metrics generator 221. Metric-specific pain scores corresponding to pain-relief electrostimulation applied according to an electrode configuration involving various candidate electrodes may be determined, such as illustrated in FIG. 4B. A composite pain score is computed using a combination of the metric-specific pain scores corresponding to the EEG parameters evaluated.

In an example, the composite pain score may be computed as a sum or weighted sum of the metric-specific pain scores. Composite pain scores may similarly computed for pain-relief electrostimulation according to other electrode configurations. The composite pain scores associated with the electrode configurations included in the stimulation protocol may be presented to the patient or a clinician.

At 740, the composite pain scores associated with the electrode configurations included in the stimulation protocol may be compared to each other. At 750, one or more active electrodes may then be selected based on the comparison. The selected one or more active electrodes correspond to respective pain scores less than pain scores associated with other candidate electrodes different from the selected one or more active electrodes. In an example, one or more candidate electrodes that correspond to the lowest composite pain score may be selected, indicating the highest effectiveness in pain reduction.

Alternatively, a metric-specific pain reduction score may be determined for each signal metric at 730, where a pain reduction score of "1" indicates desirable pain reduction effect, and a pain reduction score of "0" indicates undesirable pain reduction effect. A composite pain reduction score may be computed using a combination of the metric-specific pain reduction scores. Composite pain reduction scores associated with the electrode configurations included in the stimulation protocol may be compared to each other at 740. One or more electrodes that correspond to the highest composite pain reduction score among the candidate electrodes indicate the highest effectiveness in pain reduction, and may be selected at 750 as active electrodes for delivering electrostimulation energy.

The method 700 for selecting active electrodes based on pain scores may be modified for selecting, or determining values of, one or more other therapy parameters, including: electrode energy fractionalization which defines amount of current, voltage, or energy assigned to each active electrode and thereby determines spatial distribution of the modulation field; temporal modulation parameters such as pulse amplitude, pulse width, pulse rate, or burst intensity; morphological modulation parameters respectively defining one or more portions of stimulation waveform morphology such as amplitude of different phases or pulses included in a stimulation burst, among others. The disclosed method may also be used in selecting one or more active therapy regimes from a plurality of candidate therapy regimes each involving a combination of multiple therapy parameters such as electrode selection, energy fractionalization, waveform temporal and morphological parameters. For example, in an automated closed-loop pain therapy or clinician programmed pain therapy, a particular value for a specific therapy parameter, or a particular therapy regime, may be selected and programmed to the IPG 411 for delivering electrostimulation therapy to relieve patient pain.

Figure 8:
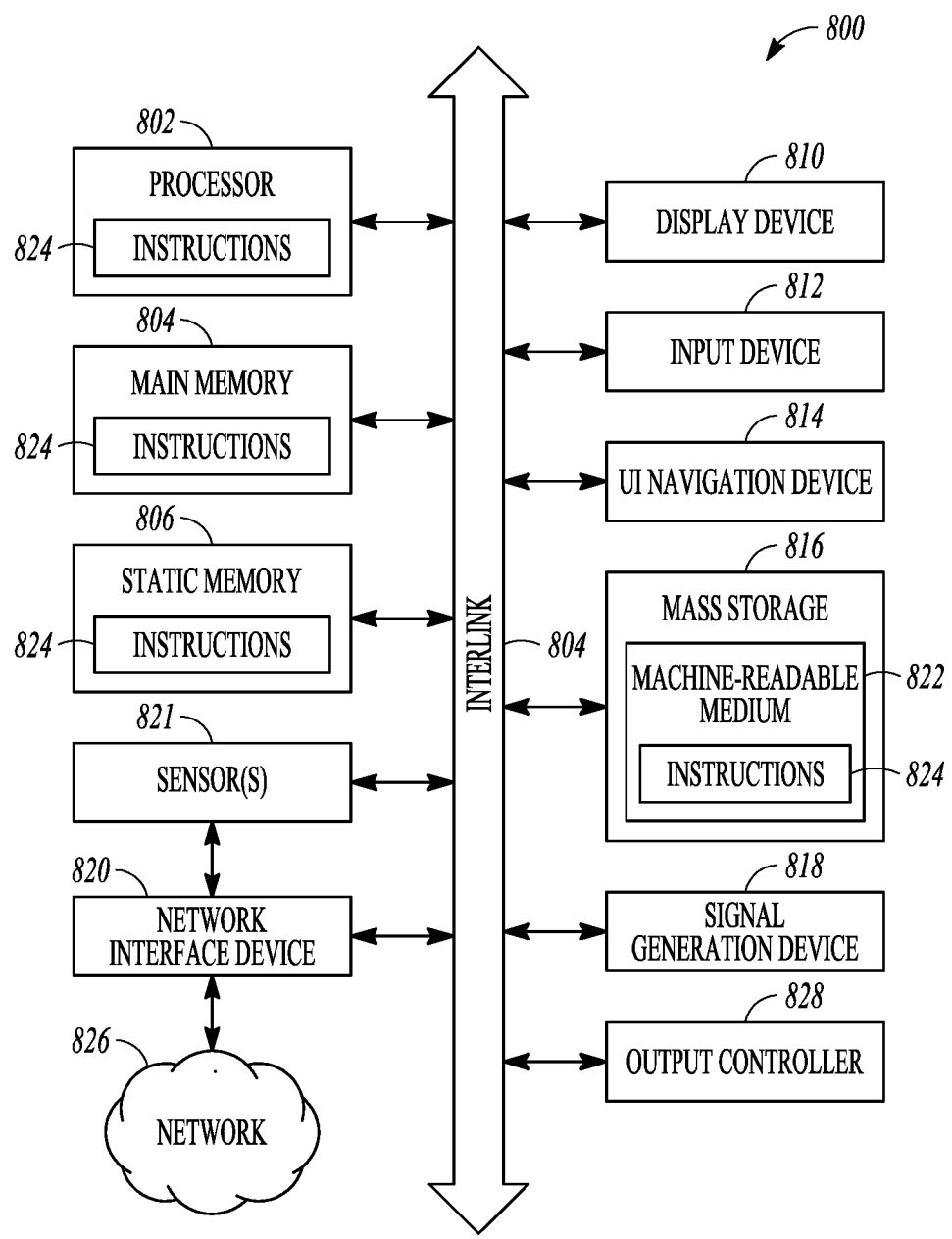
FIG. 8 illustrates, by way of example of not limitation, a block diagram of an example machine upon which any one or more of the techniques discussed herein may perform.

FIG. 8 illustrates generally a block diagram of an example machine 800 upon which any one or more of the techniques (e.g., methodologies) discussed herein may perform. Portions of this description may apply to the computing framework of various portions of the LCP device, the IND, or the external programmer.

In alternative embodiments, the machine 800 may operate as a standalone device or may be connected (e.g., networked) to other machines. In a networked deployment, the machine 800 may operate in the capacity of a server machine, a client machine, or both in server-client network environments. In an example, the machine 800 may act as a peer machine in peer-to-peer (P2P) (or other distributed)

network environment. The machine 800 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 800 may include a hardware processor 802 (e.g., a central processing unit (CPU), a graphics processing unit (GPU), a hardware processor core, or any combination thereof), a main memory 804 and a static memory 806, some or all of which may communicate with each other via an interlink (e.g., bus) 808. The machine 800 may further include a display unit 810 (e.g., a raster display, vector display, holographic display, etc.), an alphanumeric input device 812 (e.g., a keyboard), and a user interface (UI) navigation device 814 (e.g., a mouse). In an example, the display unit 810, input device 812 and UI navigation device 814 may be a touch screen display. The machine 800 may additionally include a storage device (e.g., drive unit) 816, a signal generation device 818 (e.g., a speaker), a network interface device 820, and one or more sensors 821, such as a global positioning system (GPS) sensor, compass, accelerometer, or other sensor. The machine 800 may include an output controller 828, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 816 may include a machine readable medium 822 on which is stored one or more sets of data structures or instructions 824 (e.g., software) embodying or utilized by any one or more of the techniques or functions described herein. The instructions 824 may also reside, completely or at least partially, within the main memory 804, within static memory 806, or within the hardware processor 802 during execution thereof by the machine 800. In an example, one or any combination of the hardware processor 802, the main memory 804, the static memory 806, or the storage device 816 may constitute machine readable media.

While the machine readable medium 822 is illustrated as a single medium, the term "machine readable medium" may include a single medium or multiple media (e.g., a centralized or distributed database, and/or associated caches and servers) configured to store the one or more instructions 824.

The term "machine readable medium" may include any medium that is capable of storing, encoding, or carrying instructions for execution by the machine 800 and that cause the machine 800 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 824 may further be transmitted or received over a communications network 826 using a transmission medium via the network interface device 820 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 820 may include one or more physical jacks (e.g., Ethernet, coaxial, or phone jacks) or one or more antennas to connect to the communications network 826. In an example, the network interface device 820 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 800, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system for managing pain of a patient, the system comprising:
    a sensor circuit coupled to one or more physiological sensors and configured to sense from the patient at least one physiological signal indicative of patient brain activity;
    a plurality of candidate electrodes configured to couple to an electrostimulator;
    a pain analyzer circuit coupled to the sensor circuit, the pain analyzer circuit configured to:
        generate, from each of the sensed at least one physiological signal indicative of the patient brain activity, one or more signal metrics indicative of strength or a pattern of brain electromagnetic activity associated with pain; and
        generate, for each of the plurality of candidate electrodes, a pain score using the generated one or more signal metrics;
    a controller circuit coupled to the pain analyzer circuit, the controller circuit configured to select, from the plurality of candidate electrodes, one or more active electrodes based on the pain scores; and
    an output unit configured to output the pain scores to a user.

2. The system of claim 1, further comprising:
    the electrostimulator, wherein the electrostimulator is configured to generate electrostimulation energy to treat pain; and
    wherein the controller circuit is coupled to the electrostimulator, the controller circuit configured to control the electrostimulator to deliver a pain therapy and to control the electrostimulation energy generated by the electrostimulator according to the pain score.

3. The system of claim 2, wherein the controller circuit is further configured to
    control the electrostimulator to deliver the pain therapy using the selected one or more active electrodes.

4. The system of claim 2, wherein:
    the sensor circuit is configured to sense a brain activity signal during electrostimulation delivered to the patient using one of the plurality of candidate electrodes;
    the pain analyzer circuit is configured to generate one or more brain activity signal metrics using the sensed brain activity signal, and to generate a composite pain score for the one of the plurality of candidate electrodes using metric-specific pain scores for the generated one or more brain activity signal metrics; and
    the control circuit is configured to select one or more active electrodes corresponding to respective pain scores less than pain scores associated with other candidate electrodes different from the selected one or more active electrodes.

5. The system of claim 2, wherein the controller circuit is further configured to determine electrostimulation energy fractionalization for the one or more active electrodes based on the pain scores.

6. The system of claim 2, wherein the electrostimulator is further configured to deliver at least one of:
    a spinal cord stimulation;
    a brain stimulation; or
    a peripheral nerve stimulation.

7. The system of claim 1, wherein the at least one physiological signal includes one or more electroencephalography (EEG) signals each recorded at a brain region of interest.

8. The system of claim 7, wherein:
    the one or more physiological sensors include one or more electrodes disposed on a lead configured to be implanted in a patient brain; and
    the sensor circuit is configured to sense the one or more EEG signals via the one or more electrodes disposed on the lead.

9. The system of claim 8, wherein the one or more electrodes disposed on the lead are further configured to deliver electrostimulation energy to treat pain.

10. The system of claim 7, wherein:
    the one or more physiological sensors include one or more wearable sensors communicatively coupled to the sensor circuit, the one or more wearable sensors configured to be removably worn on a patient head; and
    the sensor circuit is configured to sense the one or more EEG signals via the one or more wearable sensors.

11. The system of claim 1, wherein the pain analyzer circuit is further configured to generate the pain score associated with a candidate electrode using a combination of a plurality of the signal metrics weighted by their respective weight factors.

12. The system of claim 2, further comprising an implantable neuromodulator device that includes one or more of the sensor circuit, the pain analyzer circuit, or the electrostimulator.

13. A method for managing pain of a patient using an implantable neuromodulator device (IND), the method comprising:
    sensing at least one physiological signal from the patient via a sensor circuit, the at least one physiological signal indicative of patient brain activity;
    generating, from each of the sensed at least one physiological signal indicative of the patient brain activity, one or more signal metrics indicative of strength or a pattern of brain electromagnetic activity associated with pain;
    generating, for each of a plurality of candidate electrodes, a pain score based on the generated one or more signal metrics;
    selecting, from the plurality of candidate electrodes, one or more active electrodes based on the pain scores; and
    outputting the pain scores to a user.

14. The method of claim 13, further comprising delivering a pain therapy via the IND, the pain therapy including electrostimulation energy determined according to the pain score.

15. The method of claim 14, further comprising delivering the pain therapy using the selected one or more active electrodes.

16. The method of claim 15, wherein:
sensing at least one physiological signal includes sensing a brain activity signal during electrostimulation delivered to the patient using one of the plurality of candidate electrodes;
generating one or more signal metrics includes generating one or more brain activity signal metrics using the sensed brain activity signal;
generating pain score includes generating a composite pain score for the one of the plurality of candidate electrodes using metric-specific pain scores for the generated one or more brain activity signal metrics; and
selecting one or more active electrodes includes one or more electrodes with respective pain scores less than pain scores associated with other candidate electrodes different from the selected one or more active electrodes.

17. The method of claim 15, further comprising determining electrostimulation energy fractionalization for the one or more active electrodes based on the pain score.

18. The method of claim 13, wherein the at least one physiological signal includes one or more electroencephalography (EEG) signals each recorded at a brain region of interest via an implantable or wearable sensor.

19. The method of claim 18, further comprising:
sensing the one or more EEG signals via one or more electrodes disposed on a lead implanted in a patient brain; and
delivering electrostimulation energy to treat pain via the one or more electrodes disposed on the lead.

20. The method of claim 13, wherein generating the pain score associated with a candidate electrode includes using a combination of a plurality of the signal metrics weighted by their respective weight factors.

* * * * *